United States Patent
Shadduck et al.

(10) Patent No.: US 10,835,287 B2
(45) Date of Patent: Nov. 17, 2020

(54) FLUID SKIN TREATMENT SYSTEMS AND METHODS

(71) Applicant: John H. Shadduck, Menlo Park, CA (US)

(72) Inventors: John H. Shadduck, Menlo Park, CA (US); Benedek Orczy-Timko, Budapest (HU)

(73) Assignee: John H. Shadduck, Menlo Park, CA (US)

( * ) Notice: Subject to any disclaimer, the term of this patent is extended or adjusted under 35 U.S.C. 154(b) by 0 days.

(21) Appl. No.: 16/690,798

(22) Filed: Nov. 21, 2019

(65) Prior Publication Data

US 2020/0085470 A1    Mar. 19, 2020

Related U.S. Application Data

(63) Continuation of application No. 15/961,494, filed on Apr. 24, 2018, now Pat. No. 10,524,835.

(Continued)

(51) Int. Cl.

| | |
|---|---|
| *A61B 17/54* | (2006.01) |
| *A61M 1/00* | (2006.01) |
| *A61H 23/02* | (2006.01) |
| *A61N 5/06* | (2006.01) |
| *A61B 17/32* | (2006.01) |

(Continued)

(52) U.S. Cl.
CPC .... *A61B 17/545* (2013.01); *A61B 17/320068* (2013.01); *A61B 17/54* (2013.01); *A61H 23/02* (2013.01); *A61M 1/0064* (2013.01); *A61N 1/18* (2013.01); *A61N 5/0616* (2013.01); *A61N 7/00* (2013.01); *A61B 2017/00398* (2013.01); *A61B 2017/00402* (2013.01); *A61B 2017/00415* (2013.01); *A61B 2017/00761* (2013.01); *A61B 2017/00876* (2013.01); *A61B 2017/308* (2013.01); *A61B 2017/320004* (2013.01); *A61B 2017/320028* (2013.01); *A61B 2217/005* (2013.01); *A61H 7/005* (2013.01); *A61H 23/0218* (2013.01); *A61H 23/0263* (2013.01); *A61H 2230/655* (2013.01); *A61M 35/00* (2013.01); *A61M 35/003* (2013.01); *A61N 1/0464* (2013.01); *A61N 1/328* (2013.01); *A61N 2005/0651* (2013.01); *A61N 2005/0654* (2013.01); *A61N 2007/0034* (2013.01); *A61N 2007/0073* (2013.01)

(58) Field of Classification Search
CPC ......... A61B 17/545; A61B 17/320016–32002; A61B 2017/320024–320028; A61B 2017/00747; A61B 2017/00761; A61B 2017/320004; A61B 17/3203; A61H 7/005; A61H 9/0021; A61H 9/0028
See application file for complete search history.

(56) References Cited

U.S. PATENT DOCUMENTS

| | | |
|---|---|---|
| 2001/0037118 A1 | 11/2001 | Shadduck |
| 2004/0092959 A1 | 5/2004 | Bernaz |

(Continued)

*Primary Examiner* — Katrina M Stransky
*Assistant Examiner* — Brigid K Byrd
(74) *Attorney, Agent, or Firm* — Levine Bagade Han LLP

(57) ABSTRACT

Devices and methods for dermatology and more particularly to fluid enhanced skin treatment system for skin rejuvenation that can use an abrasive probe for removing epidermal layers while contemporaneously providing for the infusion of therapeutic fluids into the skin.

9 Claims, 24 Drawing Sheets

Related U.S. Application Data

(60) Provisional application No. 62/489,461, filed on Apr. 25, 2017.

(51) Int. Cl.

| | | |
|---|---|---|
| *A61N 1/18* | (2006.01) | |
| *A61N 7/00* | (2006.01) | |
| *A61H 7/00* | (2006.01) | |
| *A61B 17/00* | (2006.01) | |
| *A61B 17/30* | (2006.01) | |
| *A61N 1/32* | (2006.01) | |
| *A61M 35/00* | (2006.01) | |
| *A61N 1/04* | (2006.01) | |

(56) References Cited

U.S. PATENT DOCUMENTS

| | | |
|---|---|---|
| 2005/0277950 A1 | 12/2005 | Pilcher et al. |
| 2006/0047234 A1 | 3/2006 | Glucksman et al. |
| 2007/0156124 A1* | 7/2007 | Ignon ............... A61M 35/003 606/9 |
| 2009/0031871 A1* | 2/2009 | Malandain ......... A61B 17/1615 83/53 |
| 2009/0157094 A1 | 6/2009 | Yeshurun et al. |
| 2013/0158547 A1 | 6/2013 | David |
| 2013/0197552 A1* | 8/2013 | O'Brien, II ...... A61B 17/32002 606/170 |
| 2015/0088050 A1* | 3/2015 | Chang ............... A61M 37/0092 604/20 |
| 2016/0038183 A1 | 2/2016 | Ignon et al. |
| 2018/0303515 A1 | 10/2018 | Shadduck et al. |

\* cited by examiner

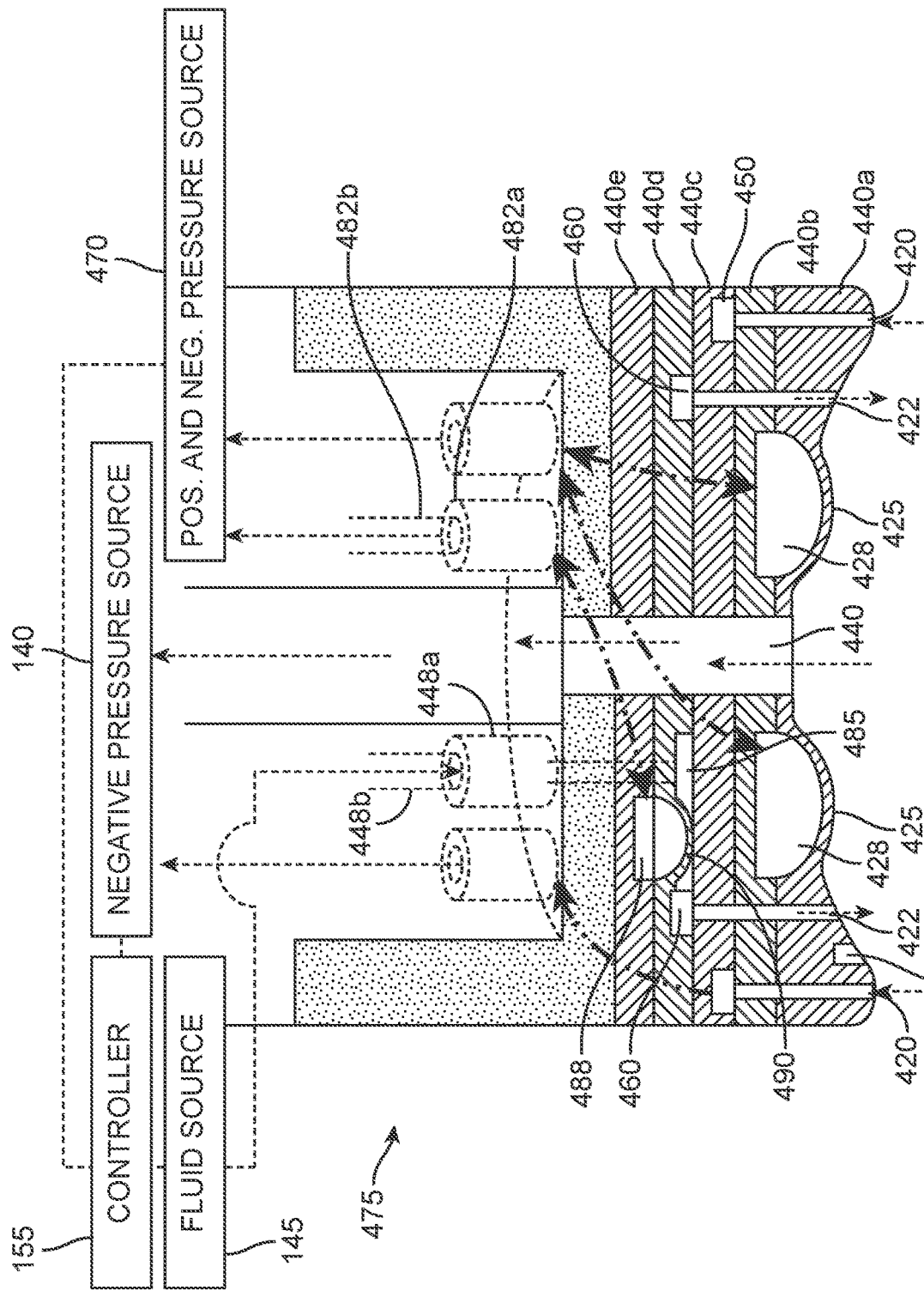

FLUID SKIN TREATMENT SYSTEMS AND METHODS

CROSS-REFERENCE TO RELATED APPLICATION

This application is a continuation of U.S. patent application Ser. No. 15/961,494 filed Apr. 24, 2018, which claims benefit of priority to U.S. Provisional Application No. 62/489,461 filed Apr. 25, 2017, the entirety of each of which is incorporated by reference.

FIELD OF THE INVENTION

The present invention relates to devices for dermatology and more particularly to fluid enhanced skin treatment system for skin rejuvenation that can optionally use an abrasive probe for removing epidermal layers while contemporaneously providing for the infusion of therapeutic fluids into the skin.

BACKGROUND OF THE INVENTION

Dermatologists and plastic surgeons have used various methods for removing superficial skin layers to cause the growth of new skin layers (i.e., commonly described as skin resurfacing techniques) since the early 1900's. Early skin resurfacing treatments used an acid such as phenol to etch away surface layers of a patient's skin that contained damage to thereafter be replaced by new skin. The term damage when referring to a skin disorder is herein defined as any cutaneous defect, e.g., including but not limited to rhytides, hyperpigmentation, acne scars, solar elastosis, other dyschromias, stria distensae, seborrheic dermatitis.

Following the removal of surface skin layers at a particular depth, no matter the method of skin removal, the body's natural wound-healing response begins to regenerate the epidermis and underlying wounded skin layers. The new skin layer will then cytologically and architecturally resemble a younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis, and (iii) deep resurfacing treatments that remove tissue to the depth of the reticular dermis.

Modern techniques for skin layer removal include: $CO_2$ laser resurfacing which falls into the category of a deep resurfacing treatment; Erbium laser resurfacing which generally is considered a medium-depth treatment; mechanical dermabrasion using high-speed abrasive wheels which results in a medium-depth or deep resurfacing treatment; and chemical peels which may range from a superficial to a deep resurfacing treatment, depending on the treatment parameters. A recent treatment, generally called micro-dermabrasion, has been developed that uses an air-pressure source to deliver abrasive particles directly against a patient's skin at high-velocities to abrade away skin layers. Such a micro-dermabrasion modality may be likened to sandblasting albeit at velocities that do no cause excess pain and discomfort to the patient. Micro-dermabrasion as currently practiced falls into the category of a superficial resurfacing treatment.

A superficial exfoliation, peel or abrasion removes some or all of the epidermis may be suited for treating very light rhytides. Such a superficial exfoliation is not effective in treating many forms of damage to skin. A medium-depth resurfacing treatment that extends into the papillary dermis can treat many types of damage to skin. Deep resurfacing treatments, such as $CO_2$ laser treatments, that extend well into the reticular dermis causes the most significant growth of new skin layers but carry the risk of scarring unless carefully controlled.

It is useful to briefly explain the body's mechanism of actually resurfacing skin in response to the removal of a significant depth of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticular dermis, which is sustained by angiogenesis and protected anteriorly by the reforming epithelial layer. The new extracellular matrix is largely composed of collagen fibers (particularly Types I and III) which are laid down in compact parallel arrays. It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal architecture of the dermal layers. It is well recognized that there will be a clinical improvement in the condition and appearance of a patient's skin when a more normal architecture is regenerated by the body's wound-healing response. Of most significance to a clinical improvement is skin is the creation of denser parallel collagen aggregates with decreased periodicity (spacing between fibrils). The body's wound-healing response is responsible for synthesis of these collagen aggregates. In addition to the body's natural wound healing response, adjunct pharmaceutical treatments that are administered concurrent with, or following, a skin exfoliations can enhance the development of collagen aggregates to provide a more normal dermal architecture in the skin—the result being a more youthful appearing skin.

The deeper skin resurfacing treatments, such as laser ablation, chemical peels and mechanical dermabrasion have drawbacks. The treatments are best used for treatments of a patient's face and may not be suited for treating other portions of a patient's body. For example, laser resurfacing of a patient's neck or decolletage may result in post-treatment pigmentation disorders. All the deep resurfacing treatments are expensive, require anesthetics, and must be performed in a clinical setting. Perhaps, the most significant disadvantage to deep resurfacing treatments relates to the post-treatment recovery period. It may require up to several weeks or even months to fully recover and to allow the skin the form a new epidermal layer. During a period ranging from a few weeks to several weeks after a deep resurfacing treatment, the patient typically must wear heavy make-up to cover redness thus making the treatment acceptable only to women.

Conventional dry microdermabrasion uses a hand-held device to jet dry abrasive particles against the skin to remove cells from the epidermis to provide a younger and healthier looking appearance, remove wrinkles and improve skin tone. The superficial treatment offered by dry microdermabrasion has the advantages of being performed without anesthetics and requiring no extended post-treatment recovery period. However, such dry microdermabrasion systems do not treat deep wrinkles and dehydrates the patient's skin.

SUMMARY OF THE INVENTION

The fluid skin treatment systems and methods corresponding to the invention relate in general to the field of skin care, and the systems may be used by an individual to treat his or her own skin or can be used by a practitioner to treat a patient's skin. The systems may be used to perform dermabrasion, skin rejuvenation, cleansing and the infusion of treatment fluids into the skin.

In one variation, the system provides new modalities of fluid enhanced dermabrasion which improve upon the devices and methods disclosed by the author in U.S. Pat. Nos. 6,641,591; 7,678,120; 7,789,886, 8,066,716 and 8,337, 513, all of which are incorporated herein by this reference. A fluid enhanced microdermabrasion system includes a probe with an abrasive skin-contact surface, a negative pressure source and a treatment fluid source both in communication with the skin-contact surface. The operator translates the abrasive skin-contact surface over the patient's skin to remove an epidermal layer, and the negative pressure source suctions the skin-contact surface against the skin while at the same time drawing the treatment fluid from a source to the abraded skin surface. A combination of surface features of the skin-contact surface and the negative pressure allows the treatment fluid to penetrate surface skin layers. Such a fluid-assisted microdermabrasion treatment can remove visible lines and allow for improved absorption of topical skin treatment products.

There remains a need for a skin treatment system that can effectively rejuvenate a patient's skin, that can optionally use abrasives for removing epidermal layers and that provides an effective means for the infusion of therapeutic fluids into the skin. Further, there is a need for a system that allows for use by aestheticians in an office setting and for use at home by the patient.

BRIEF DESCRIPTION OF THE DRAWINGS

FIG. 12B is a sectional view of the working end of FIG. 11A with the valve in a closed position.

DETAILED DESCRIPTION OF THE INVENTION

Figure 1:
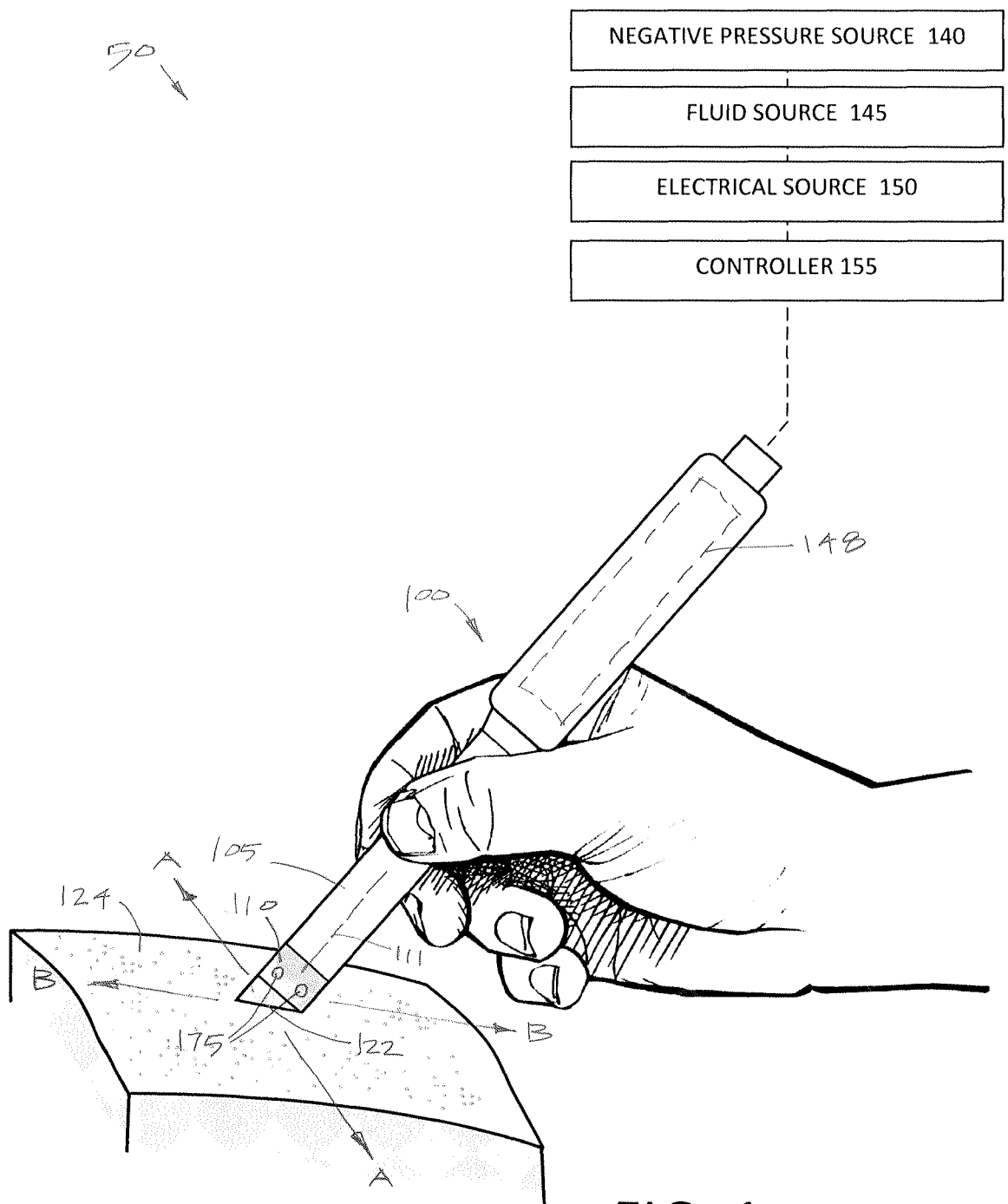
FIG. 1 is a perspective view of an embodiment of the treatment device in use being held by a human hand in relation to a patient's skin.
Figure 2:
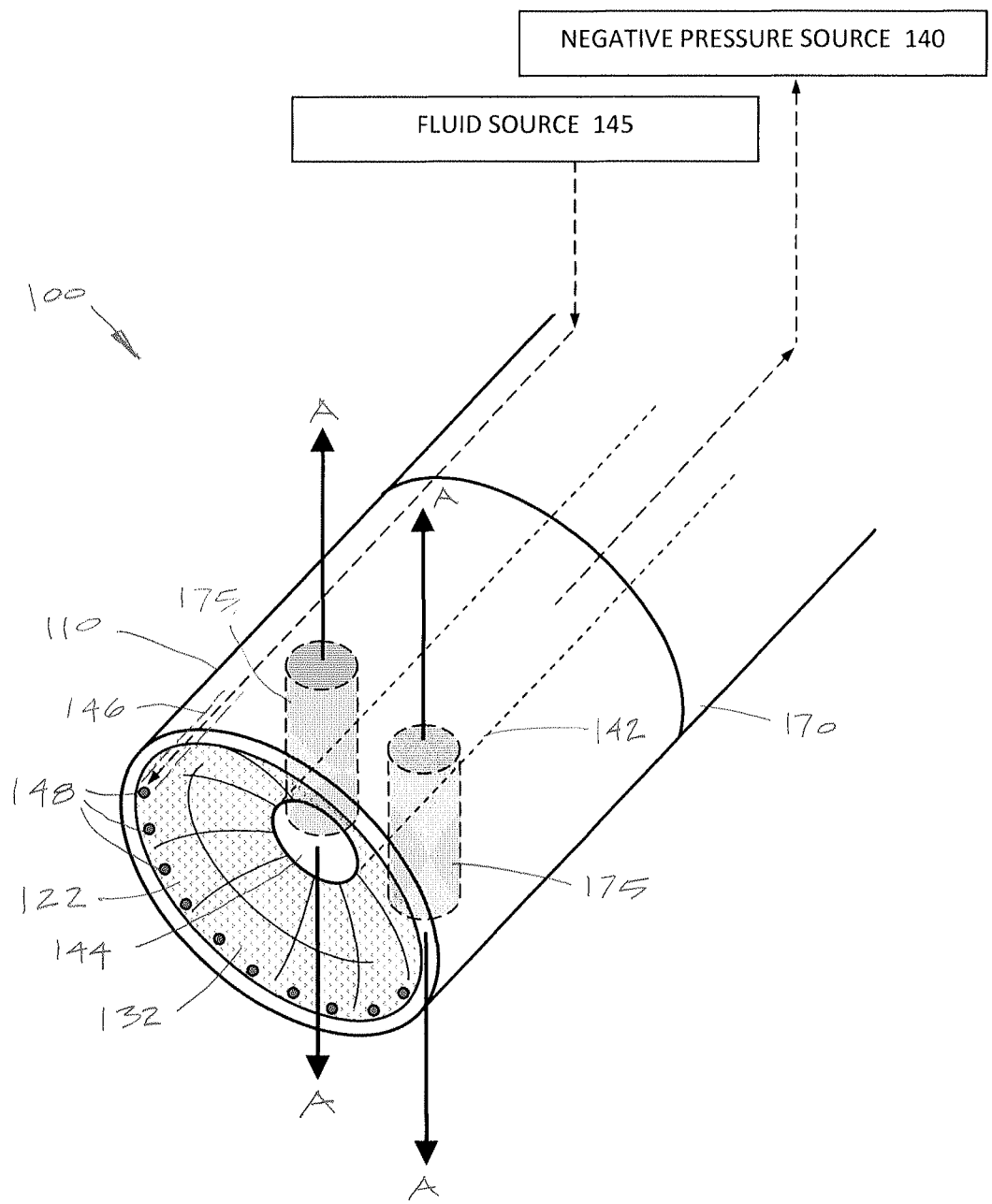
FIG. 2 is a perspective view of a working end of a device similar to that of FIG. 1 showing the location and orientation of linear actuators, fluid inflow ports and a central suction passageway in the working end.

FIGS. 1 and 2 illustrate an embodiment of the invention wherein the fluid skin treatment system 50 includes a treatment device 100 comprising a hand-held unit with an elongated shaft or body 105 that can be gripped by the operator's hand and a working end or applicator tip portion 110 with a skin contact surface 122 configured to engage a patient's skin 124 (FIG. 1). The body 105 can have any suitable dimension along axis 111 and any shape suited for gripping with a human hand or fingers, and the surface area of the skin contact surface 122 can range from about 20 mm2 to 100 cm2. Devices with smaller dimension skin contact surfaces 122 are suited for treating facial skin, and the larger skin contact surfaces 122 are adapted for treating a patient's torso, arms or legs. In one variation described below, a practitioner may use a large surface area device (see, e.g., FIG. 6B) to treat a skin of a patient's arms, legs, torso or back in a form of fluid infusion into the epidermis, skin cleansing or a chemo-detoxification therapy.

Figure 3:
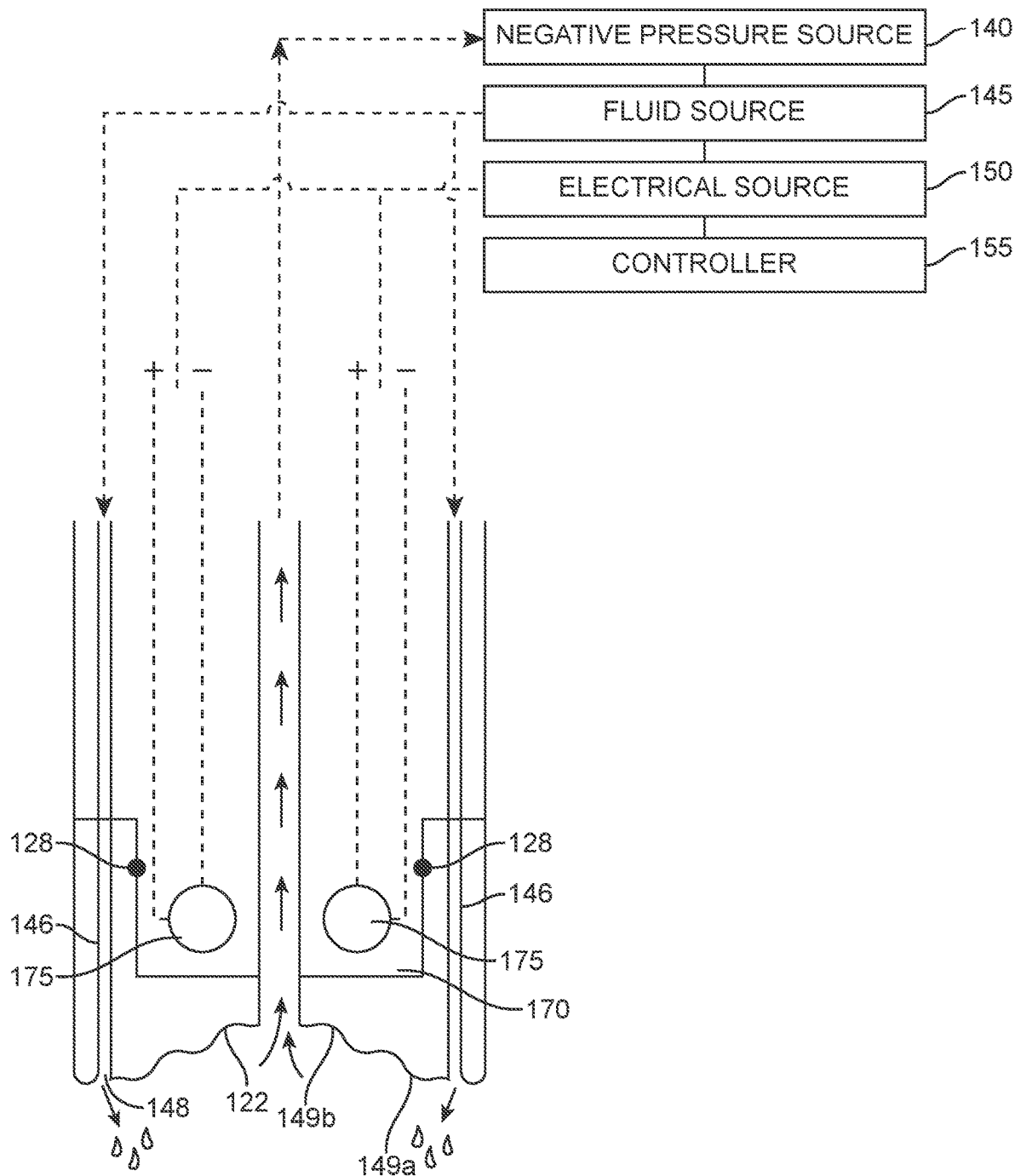
FIG. 3 is a sectional view of a working end similar to that of FIG. 2 showing the orientation of linear actuators, fluid inflow ports and a central suction passageway.

The components of device 100 as can be understood from FIGS. 1-3 include the device body 105 being fabricated of a molded plastic, metal, a combination of plastic and metal or other suitable materials. The body 105 can be disposable or re-useable, or can be a combination of disposable and non-disposable components. In the illustrated variations, the working end or applicator tip portion 110 is detachable from the device body 105 and can be coupled to the body 105 by a slip fit or friction fit with or without an o-ring 128 as can be understood from FIG. 3. Any means of detachably coupling the applicator tip 110 to the body 105 may be suitable, such as screw thread or quick-connect type fittings. In one variation, the applicator tip 110 is a substantially rigid plastic material and can be disposable. In another variation, the tip 110 is configured with at least the skin contact surface 122 comprising a soft silicone or other rubber-like material that can flex and/or compress slightly when engaging a patient's skin as will be described below.

Now referring to FIGS. 1-3, it can be seen that the system 50 includes a negative pressure source 140 that communicates with an aspiration channel 142 in the device 100 that terminates distally in an opening 144 in the skin contact surface 122. In the variation of FIG. 2, the aspiration channel 142 terminates in opening 144 in the center of skin contact surface 122, but it should be appreciated that the opening 144 can be singular or multiple and can be located or distributed anywhere in the skin contact surface 122.

The system 50 further includes a fluid source 145 that communicates with at least one flow channel 146 in the device body 110 which extend through the applicator tip 110 and terminate in a plurality of ports 148 in the skin contact surface 122 (FIG. 2). As can be seen in FIG. 2, the ports 148 are distributed around an outer perimeter of the skin contact surface 122. In this variation, the skin contact surface 122 is concave which is adapted for suctioning tissue into the concavity of the applicator tip 110. In one variation, the skin contact surface 122 can carry abrasive elements, such as diamond particles 132 embedded into the surface 122. One or more such tips 110 with abrasives can be used during a treatment of a patient's skin, with different size diamond particles in different tips for more aggressive and less aggressive dermabrasion. In a method of making an applicator tip 110, such a tip can be injection molded of a rigid plastic. Thereafter, the skin contact surface 122 can be heated to be slightly melted and then impressed within a form against diamond particles 132 which then can be somewhat embedded in the skin contact surface 122 as the plastic cools and resets. In another variation method of making an applicator tip 110, the skin contact surface 122 can be an elastomer (e.g., silicone) which can be molded into a form that carries the diamond particles will then be bonded to the surface 122. In another method, the diamond particles can be mixed with a polymer or elastomer and following a molding process, a thin layer of the polymer or elastomer can be removed (by chemical etching, sand blasting, etc) to expose the diamond particles. In another method, the diamond particles can be bonded to a molded applicator tip 110 with adhesives or bonding agents.

FIG. 1 shows the fluid source 145 being remote from the handheld device 100, but it should be appreciated that the device body 105 can be dimensioned to carry a cartridge fluid source indicated at 148 in FIG. 1.

In FIG. 1, it can be seen about the plane of the skin contact surface 122 is angled about 30 to 45° from the longitudinal axis 111 of the body 105. It should be appreciated that the plane of the skin contact surface 122 can vary from about 45° to 90° from said axis 111. For convenience, FIGS. 2-3 show the skin contact surface 122 as being perpendicular to the axis 111.

In the variation in FIG. 3, it can be seen that the skin contact surface 122 in configured with a plurality of annular ridges 149a and recesses 149b which are adapted for engaging and tensioning the patient's skin under when the device is used to abrade skin, as disclosed in the author's previous patents, for example, U.S. Pat. No. 6,641,591. The ridges may be provided with sharp edges or abrasive diamond particles 132 or other abrasive elements for abrading skin.

Referring to FIGS. 1-3, the system 50 further includes an electrical source 150 and controller 155 for actuating a mechanism to impart vibratory forces from the skin contact surface 122 to the patient's skin. In FIGS. 2-3, a device 100 corresponding to the invention includes the distal portion 170 of body 105 carrying at least one linear actuator or linear resonant actuator 175 which is adapted to provide mechanical vibratory force in a particular 'single' direction (or vector). In FIG. 2, the body 105 carries two actuators 175 which are configured to produce vibratory motion as shown by arrows AA that is perpendicular to the plane of the skin contact surface 122. The variations of FIGS. 2 and 3 shows first and second linear resonant actuators (LRAs) 175 carried within non-disposable body 105 closely adjacent to the disposable applicator tip 110 so that vibratory forces are transmitted directly to the applicator tip 110 and skin contact surface without any significant energy losses. To enhance coupling of vibratory forces between the device body 105 and the applicator tip 110, that can be engagement features such as keys, pins, or cooperating male-female elements and the like to effectively couple motion from the LRAs 175 to the skin contact surface 122 and then to the patient's skin.

As background, the forces produced by vibration motors are actually vectors, with both a direction and a magnitude. In the configurations of skin treatment devices disclosed herein corresponding to the invention, the direction of vibratory motion provide by LRAs is designed to achieve certain objectives, which can be (i) to enhance abrasion with an abrasive applicator tip 110, or (ii) to enhance fluid infusion into the patient's skin, for example, following dermabrasion.

Figure 4A:
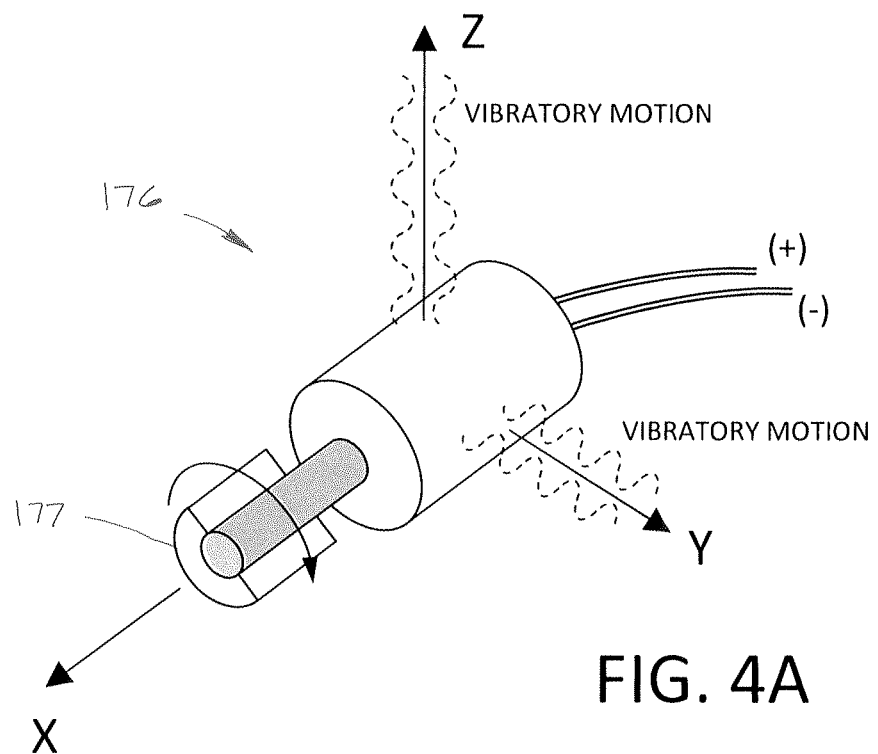
FIG. 4A is an illustration of a vibration device comprising an eccentric rotating mass (ERM) motor.

A typical type of vibration motor is an eccentric rotating mass (ERM) motor 176 as shown in FIG. 4A. This type of vibration motor operates on a direct current and carries an offset mass or non-symmetric mass 177 attached to the motor shaft. In operation, the motor rotates the eccentric weight and the centrifugal or centripetal forces are unbalanced which causes a rapid displacement of the motor resulting in as vibration. This ERM type of motor essentially then vibrates in two directions X and Y with no direct movement in the direction of the axis Z of the motor shaft. A 'coin' vibration motor works on the same principle as an article ERM motor except it is flatter and compact. The author believes that such ERM vibration motors would not be particularly effective in the present application, and therefore the use of an ERM motor is not proposed herein for several variations of skin treatment devices.

Figure 4B:
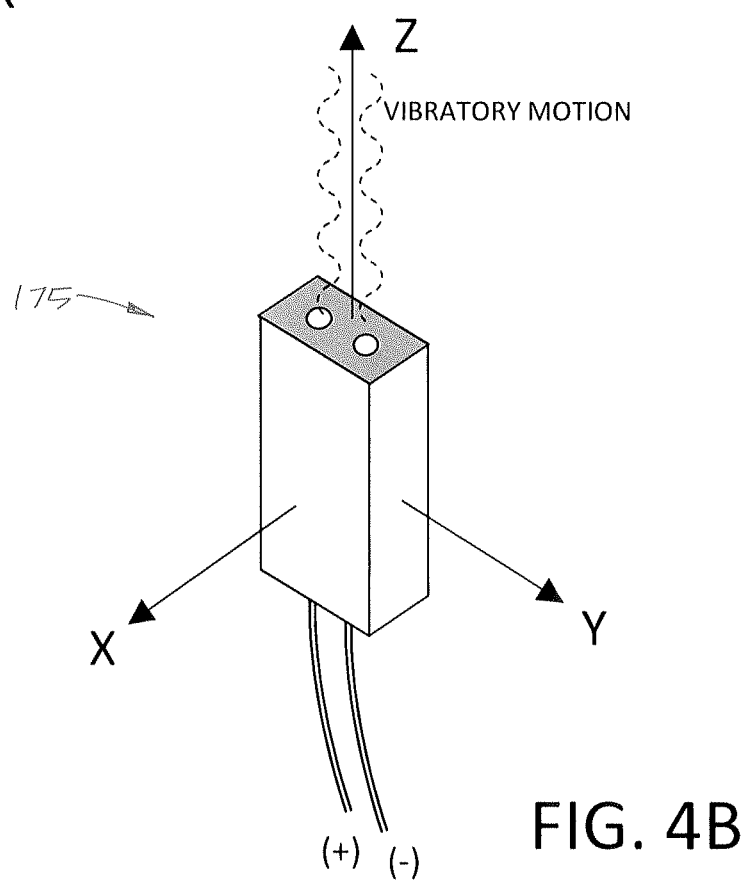
FIG. 4B is an illustration of a vibration device comprising a linear resonant actuator (LRA).

With the above background in mind, the invention herein discloses the use of linear resonant actuator or LRA 175 as shown in FIG. 4B that allows for control of the vectors (direction and magnitude) of vibratory forces applied to a patient's skin. Of particular interest, the LRAs produce vibrations much differently than ERM or eccentric rotating mass motors. An LRA comprises a magnet, a spring and a voice coil that are adapted for motor displacement. The magnet is actuated by an electromagnetic field in the voice coil, and the spring enables the magnet (that has a selected mass) to oscillate back and forth around a normal rest position maintained by the spring. Thus, it can easily understood that the magnet can be restricted to move back and forth along only one axis Z in FIG. 4B. Such an LRA is adapted to be driven by an AC drive signal. Thus, in one variation described above and shown in FIGS. 2 and 3, the LRA is mounted to generate vibratory motion substantially parallel to the patient's skin (and the skin contact surface 122) in an "abrasion mode" to move the abrasive applicator tip 110 across the surface of the skin. This form of motion parallel to the skin is advantageous compared the type of motion provided by a typical ERM motor that is not capable of generating vibratory forces in a single plane.

As can be understood from FIG. 1, the device 100 and it applicator tip 110 are also adapted to be manually moved or translated across the patient's skin at the same time the LRAs provide vibratory motion. In one variation, the device includes directions for use wherein the practitioner is instructed to move the applicator tip 110 in directions perpendicular to the direction of vibratory motion provided LRAs 175. Thus, the combination of manual translation and vibratory motion allows for very effective removal of epidermal layers. As an example, in FIG. 1, the directions of vibratory motion are indicated by arrows AA, and the direction of manual translation indicated by arrows BB.

Figure 5A:
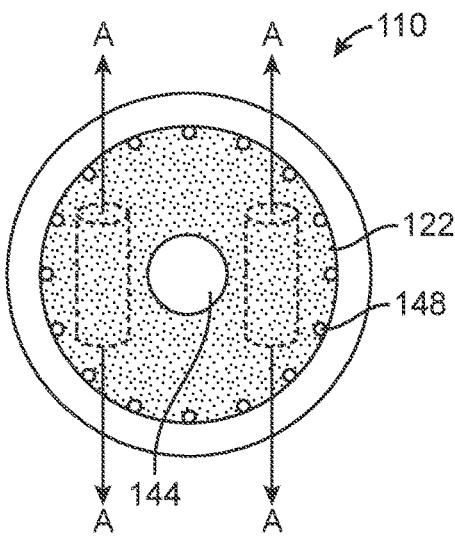
FIG. 5A is a front elevation view of the working end of FIG. 2 again showing the location and orientation of linear actuators, fluid inflow ports and a central suction passageway in the working end.
Figure 5B:
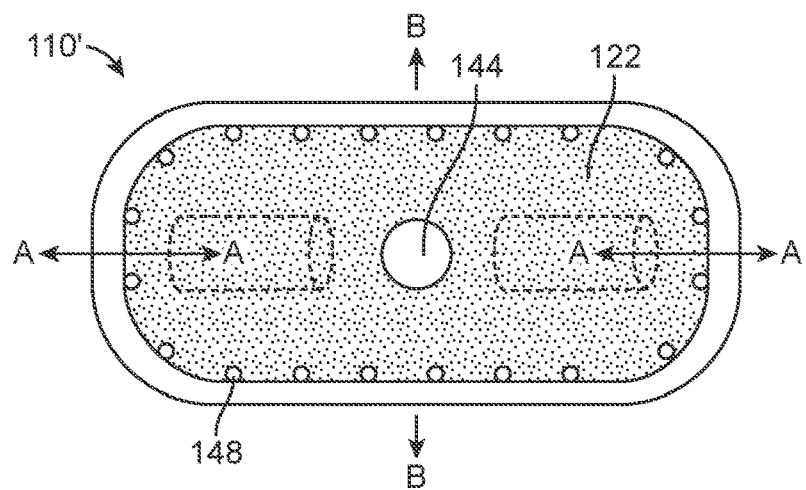
FIG. 5B is a front elevation view of another variation of a working end similar to that of FIG. 5A showing the location and orientation of linear actuators, fluid inflow ports and a central suction passageway.
Figure 5C:
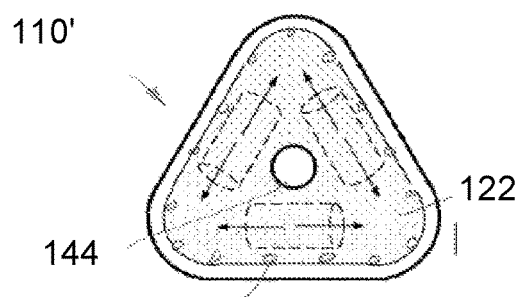
FIG. 5C is a front elevation view of another variation of a working end showing the location and orientation of linear actuators, fluid inflow ports and a central suction passageway.

FIGS. 5A-5B illustrate end view of other variations of skin contact surfaces 122 with outlines of LRAs and the direction of vibratory forces. FIG. 5A is a view of an applicator tip 110 as in FIGS. 2 and 3 and shows the direction vibratory forces AA. FIG. 5B shows a variation 110' in the shape of the skin contact surface 122 and again shows the direction of vibratory motion provided by the LRAs with arrows BB indicating the intended direction manual translation. FIG. 5C shows another variation 110" in which the LRA provides vibratory motion in multiple directions perpendicular to the axis of the device and there would not be a preferred direction of manual translation. Linear resident actuators of the type useful for the present invention can be obtained from Precision Microdrives Ltd. 105 Canterbury Court, 1 Brixton Road, London, SW9 6DE, United Kingdom.

Referring again to FIGS. 1-3, it can be understood further that the controller 155 can be configured to control the electrical source 150 that drives the LRAs, while contemporaneously controlling fluid flows from the fluid source 145 and the negative pressure source 140. In general, the variation shown in FIGS. 2 and 4 provides LRAs that can enhance skin abrasion with an abrasive applicator tip 110. The LRAs can provide sonic motion which may be in the range of 50 Hz to 1000 Hz for a skin abrasion mode of operation. The range of amplitude of the LRA can be from 0.005" to 0.25".

Figure 6A:
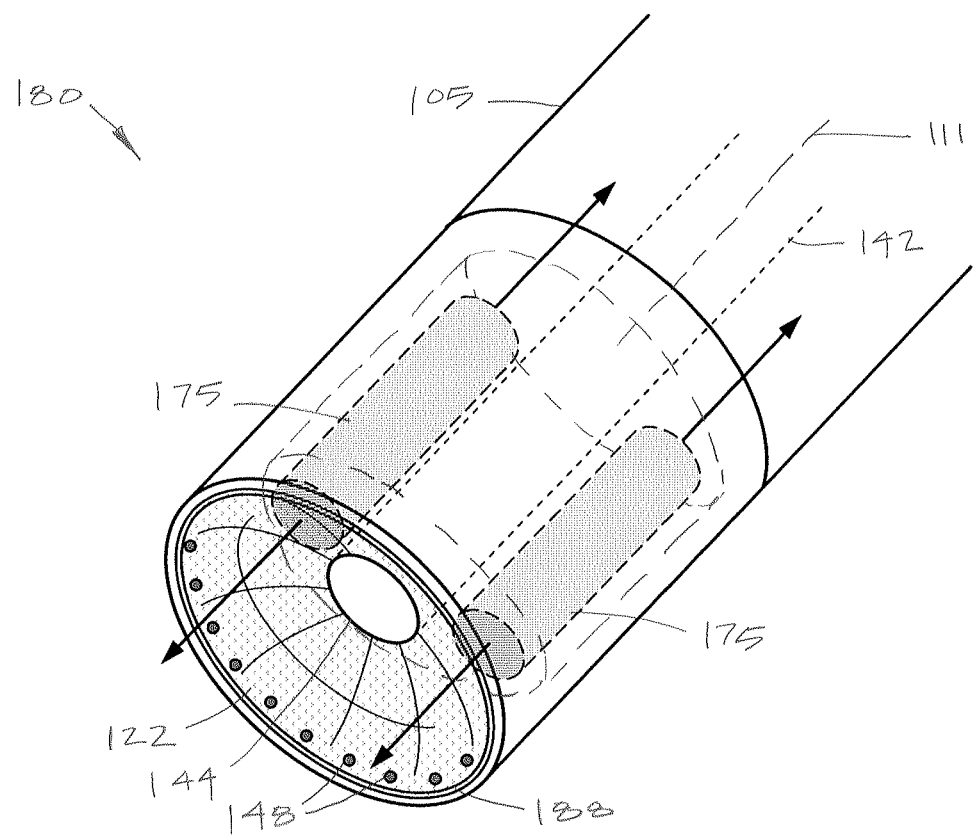
FIG. 6A is a perspective view of another variation of working end with the linear actuators configured to impart vibrational mechanical energy longitudinally relative to the longitudinal axis of the device shaft.
Figure 6B:
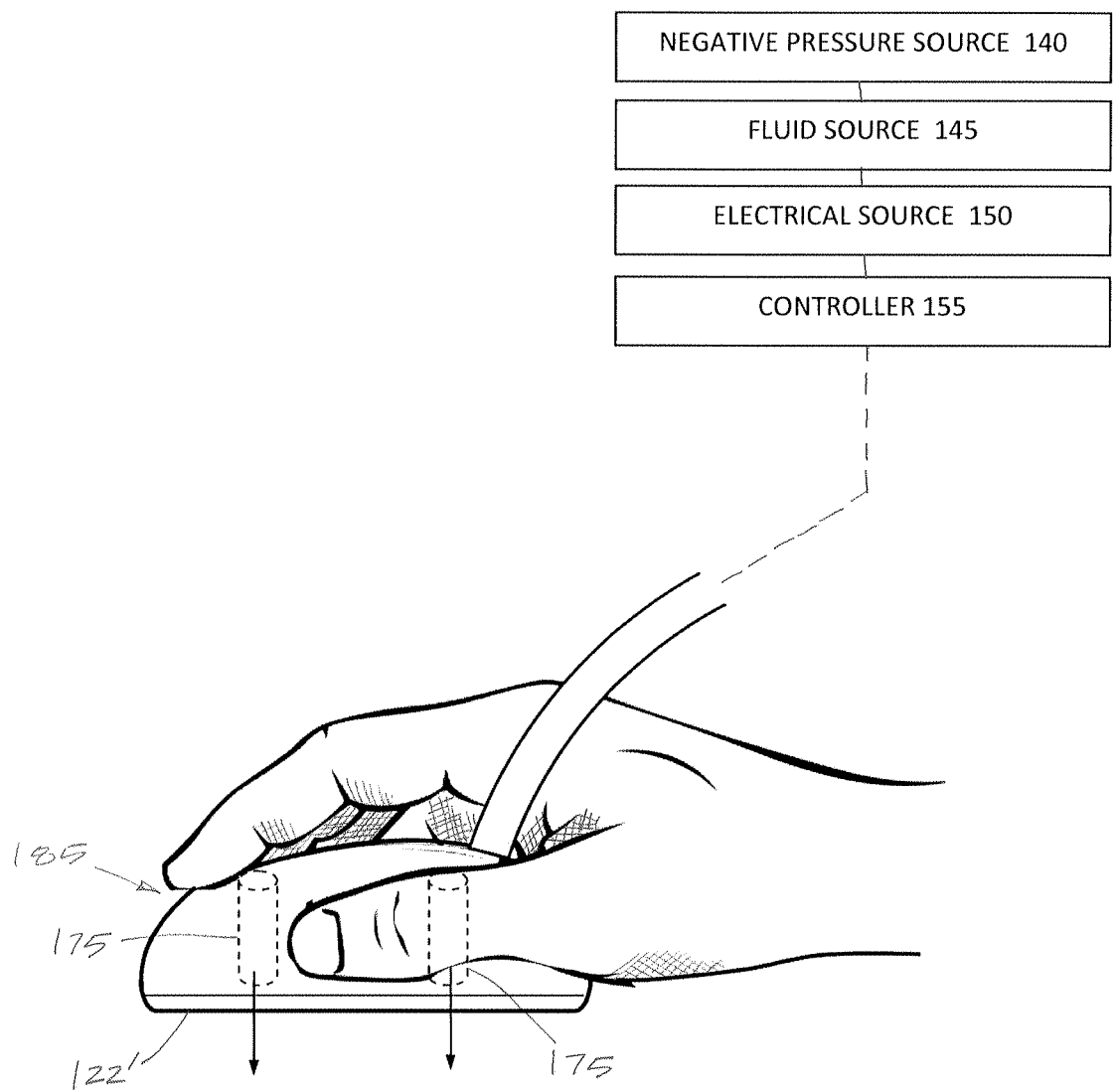
FIG. 6B is a perspective view of another embodiment of the skin treatment device and linear actuators in use being held by a human hand in relation to a patient's skin.

Now turning to FIGS. 6A and 6B, another applicator tip variation 180 is shown which uses LRAs 175 to provide a different mode of operation. In the variation shown in FIG. 6A, two LRAs are oriented substantially parallel to the axis 111 of the device body 105, or generally perpendicular to the skin contact surface 122. This applicator tip 180 may or may not have abrasive elements in the skin contact surface 122. In this variation, the LRAs 175 are adapted to operate in an "infusion mode" to infuse fluid from fluid source 145 into the patient's skin by means of vibratory forces being applied substantially perpendicular to a tensioned skin surface along with the fluid flows. FIG. 6B shows a handheld device 185 with a different form factor having a much larger skin contact surface 122' that again has at least one LRA 175 are oriented perpendicular to the skin contact surface 122'. The devices of FIGS. 6A-6B may be used following an abrasive skin treatment wherein these devices may be dedicated for use in enhancing fluid penetration into the patient's epidermis.

Figure 7A:
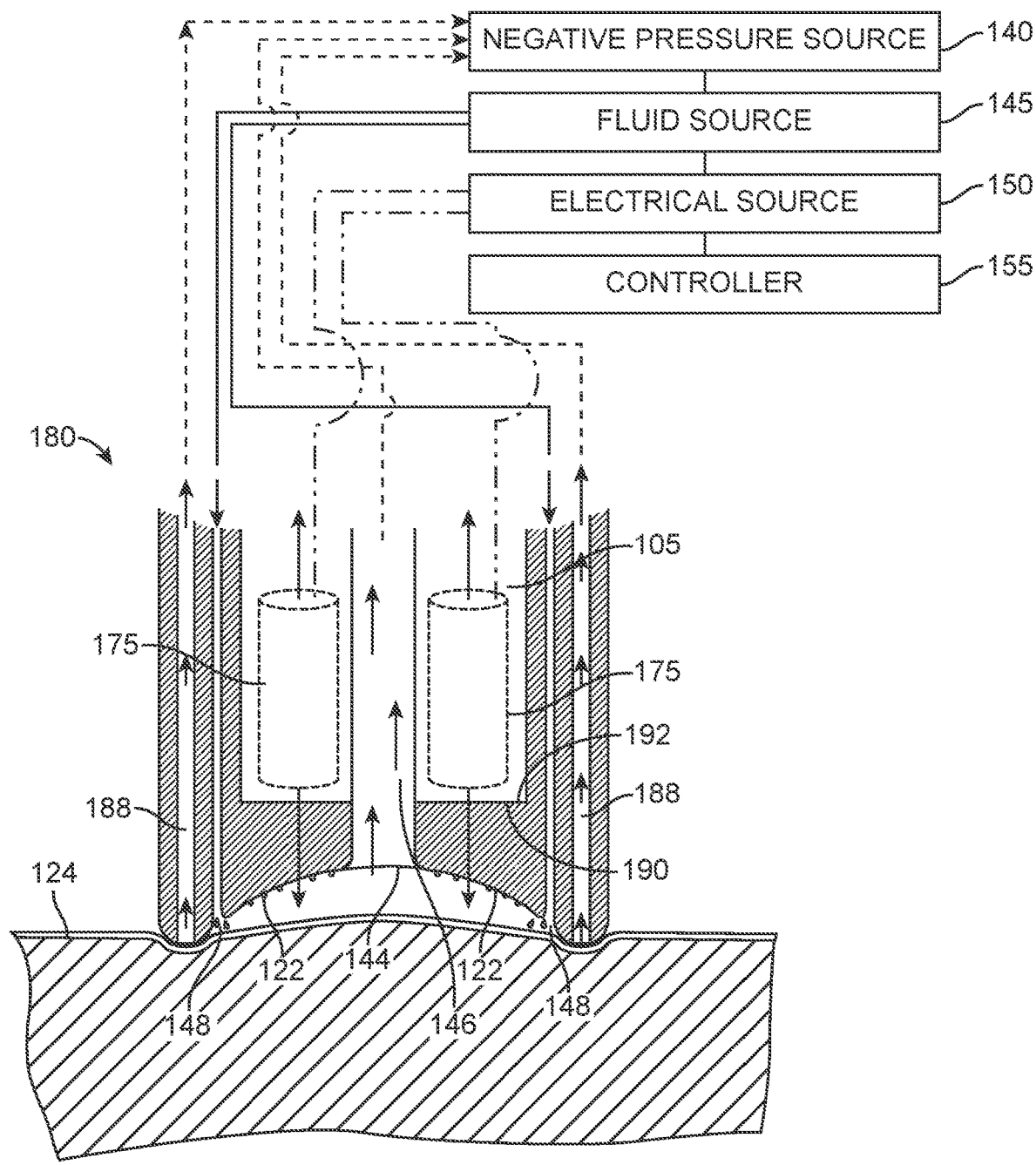
FIG. 7A is a sectional view of an initial step of using the working end of FIG. 6A to treat a patient's skin.
Figure 7B:
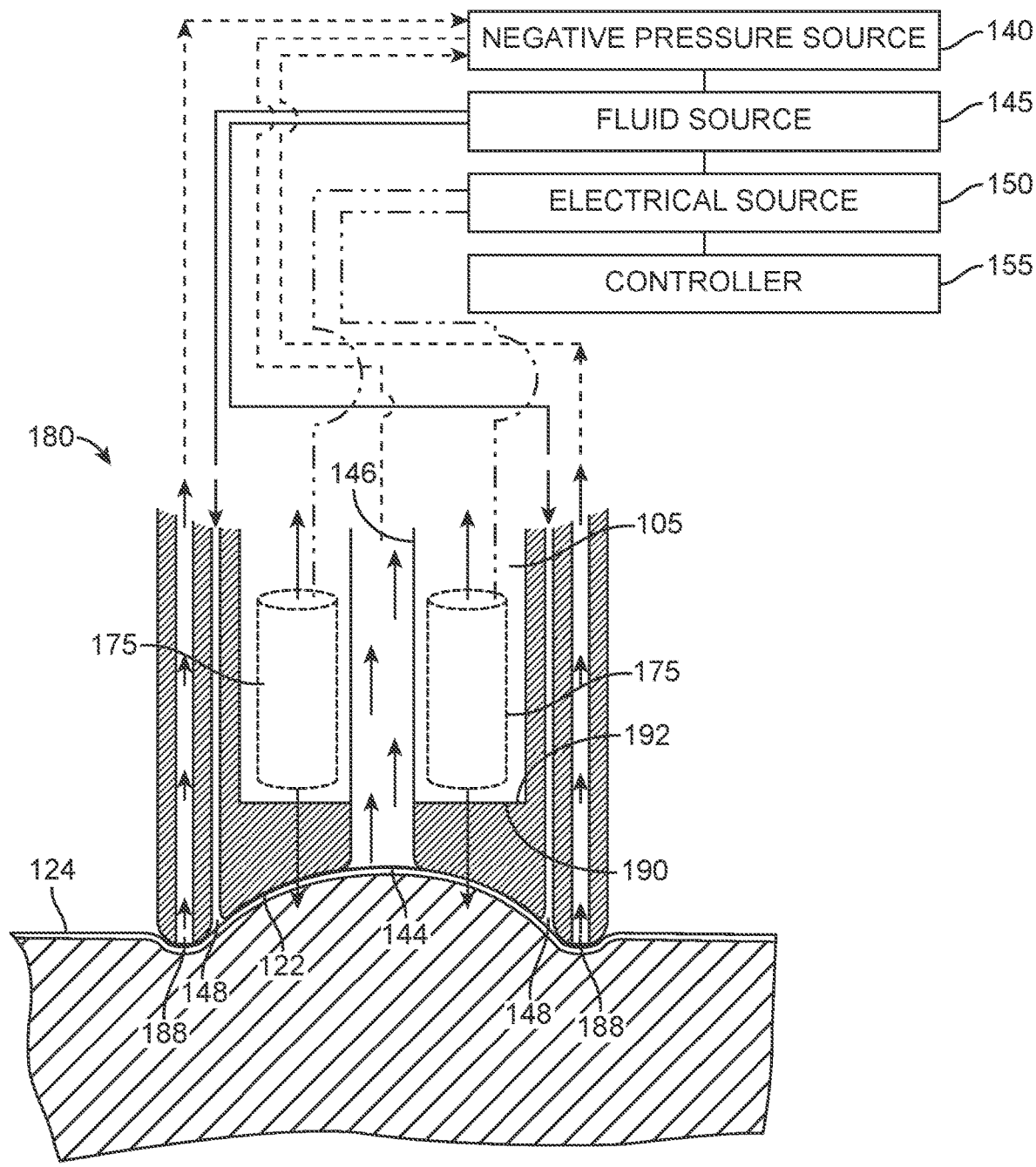
FIG. 7B is a sectional view similar to FIG. 7A showing subsequent step of actuating the negative pressure source, the fluid source and the linear actuators to treat the patient's skin.

As can be seen in FIGS. 6A and 7A, the applicator tip again has a central aspiration channel 142 communicating with central opening 144. In addition, the negative pressure source 140 communicates with a peripheral annular channel 188 (or set of ports). Thus, the patient's skin can be suctioned against the skin contact surface 122 at both the periphery and the center of the working end to capture and tension the skin surface. The central aspiration opening 144 and the peripheral aspiration channel 188 can be coupled to the same negative pressure source 140 or the controller 155 can control valves in the aspiration channels to modulate suction pressure in the ports 144 and 188. In one variation, referring to FIG. 7A, the controller 155 operates the system so that initially suction is applied through the perimeter aspiration channel 188 to engage the skins surface as shown in FIG. 7A. Thereafter, the controller 155 actuates the negative pressure source 140 to provide suction through the central opening 144 which results in stretching the skin into the concavity of the applicator tip 110 as shown in FIG. 7B. The controller 155 then further can operate an optional valve to allow fluid to flow from fluid source 145 through ports 148 to interface with the skin. The fluid flows can be provided by a positive pressure pump or can be influenced by the negative pressure at the skin surface through aspiration port 144. Finally, the controller 155 can actuate the LRAs contemporaneous with fluid flows to the skin interface, which provide mechanical force to infuse fluids into the stretched and abraded skin surface. The operator can actuate the system by a switch on the hand-held device 100 or by means of a foot switch, or another suitable switching mechanism. Thus, in FIG. 7B can be seen by picturing motion of the LRA's assistant driving fluids perpendicularly into the epidermis. It is believed that they are between motion are useful for that influence the epidermis, for example from 500 Hz to 4000 Hz.

It can be understood from the FIGS. 2-7B that the LRAs 175 are carried in the device very close to the distal end of body 105 to allow the transmission of forces directly to and through the applicator tip 180 to the patient's skin. The device is designed so that a disposable applicator tip 180 can be attached to body 105 so that surface 190 of the tip 180 interfaces with surface 192 of body 105 to allow effective force transmission from the LRAs through the tip (see FIGS. 7A-7B).

Figure 8:
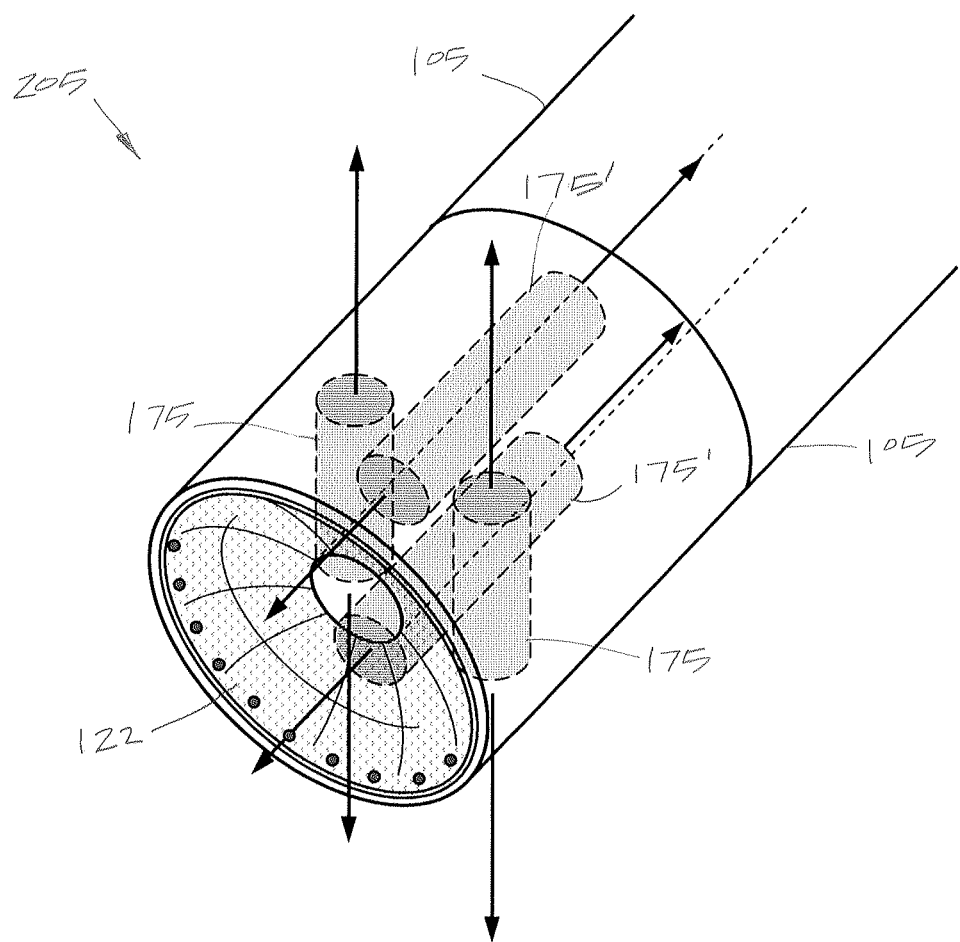
FIG. 8 is a sectional view of another variation of working end with multiple linear actuators configured to selectively impart vibrational energy to skin in a first axis and/or a second axis.

In another variation shown in FIG. 8, a device body 205 can be configured with multiple LRAs with at least one LRA 175 oriented to provide vibratory motion parallel to the skin surface for causing abrasion in an "abrasion mode" with at least one another LRA 175' oriented to provide vibratory motion substantially perpendicular to the skin surface to enhance fluid penetration into the patient's epidermis in an "infusion mode" as described above. In one system variation, the operator can select activation of the skin-parallel LRA motion or the skin-perpendicular LRA motion. In another system variation, the controller 155 can operate each LRA in pulsed intervals ranging from 0.1 seconds or more. Further, the controller 155 can be adapted to operate "abrasion mode" LRAs in a timed sequence with the "infusion mode" LRAs. The controller 155 can have presets or can be programmable to provide various overlapping or non-overlapping abrasion and infusion modes.

Figure 9:
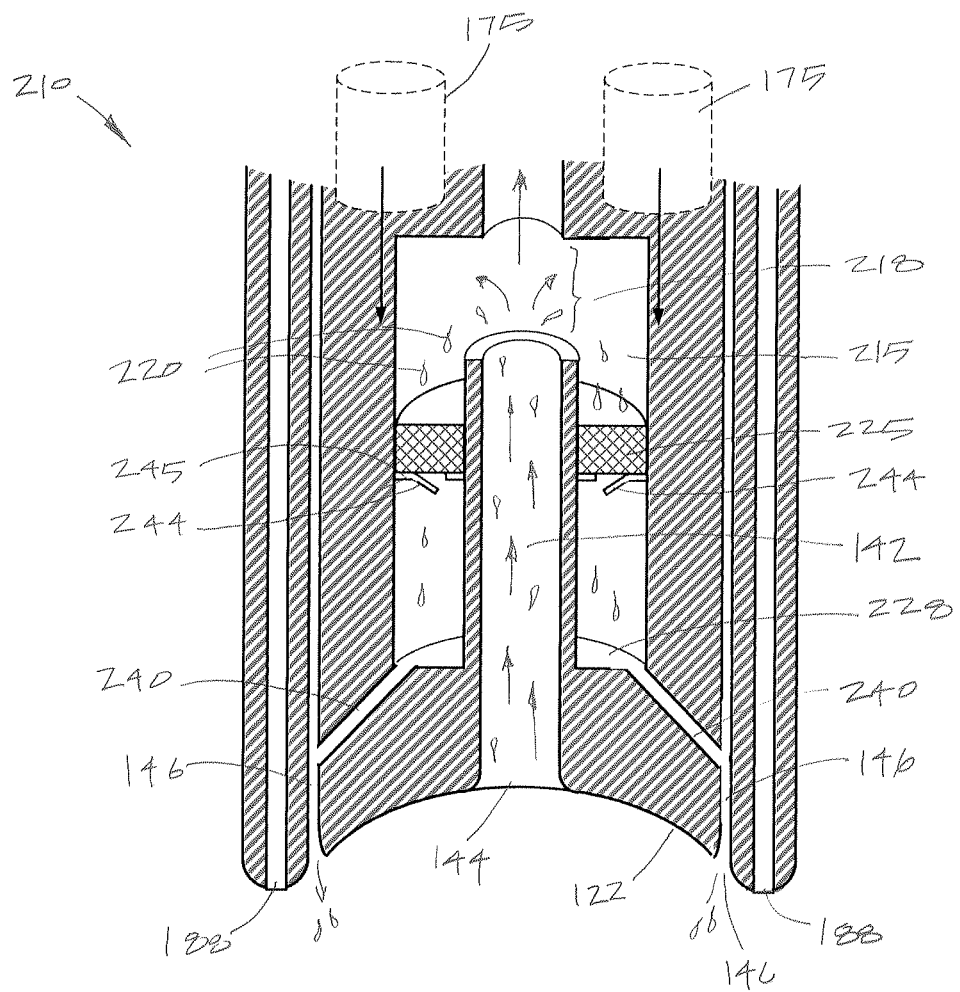
FIG. 9 is a sectional view of another variation of working end with a fluid trap and fluid recirculation mechanism.

FIG. 9 another embodiment another variation of an applicator tip 210 that includes a fluid trap for allowing the recirculation of therapeutic fluids. The applicator tip 210 of FIG. 9 is similar to the FIG. 7A, with central aspiration channel 142, peripheral aspiration channel 188 and a plurality of fluid inflow channels 148 in a concavity of the tip 210. The tip 210 can be disposable, and includes an interior collection chamber 215. As can be seen, the aspiration channel 142 extends partway through the collection chamber 215 and a gap 218 in the channel allows fluids in the outflows to separate from the aspirated gas flows. Thus, gravity will cause fluid droplets 220 to fall out of the aspiration pathway into chamber 215. The fluid droplets can pass through a filter indicated at 225 and then fall to the bottom 228 of chamber 215 and then through channels 240 back in the fluid inflow channels 148. By this means, therapeutic fluids that were not absorbed by the patient's skin may be re-introduced in to the interface with the skin for infusion therein. In one variation, shown in FIG. 9, the collection chamber 215 includes one-way valves 244, such as flaps in a silicone sheet 245 wherein aspiration pressure from negative pressure source 140 closes the valves 244 to prevent fluids or gas from being suctioned through recirculation channels 240. It can be understood that when the collected fluid reaches a certain weight in the chamber and when the operator intermittently stops operating the negative pressure source 140, then the captured fluids will fall through the one-way valves 244 into the bottom 228 of the collection chamber 215. In another variation, the controller 155 can intermittently turn off the negative pressure source 140 which will then allow the captured fluid volume to fall through the one-way valves 244 to the bottom 228 of the collection chamber 215. It can be seen in FIG. 9 that the LRA's 175 can be positioned proximate to the applicator tip 210 to provide vibratory motion as described previously. It should be appreciated that the applicator tip 210 of FIG. 9 can have any suitable dimensions to position the LRAs 175 into close proximity to the skin contact surface 122.

Figure 10:
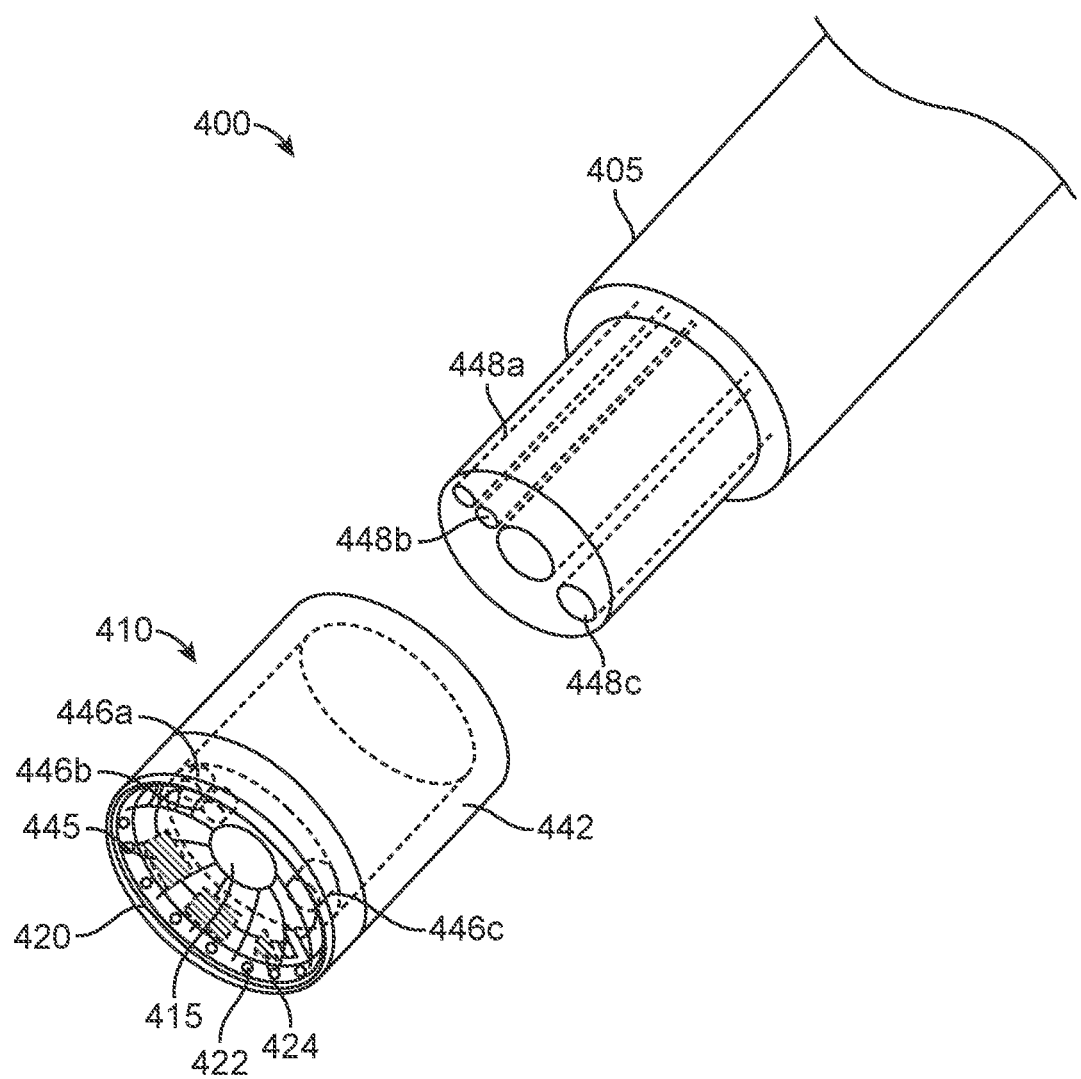
FIG. 10 is a perspective view of another variation of working end that includes a microfabricated microfluidic elastomer block with integrated channels for fluid flows and further configured with elastomeric actuators for treating a patient's skin.
Figure 11A:
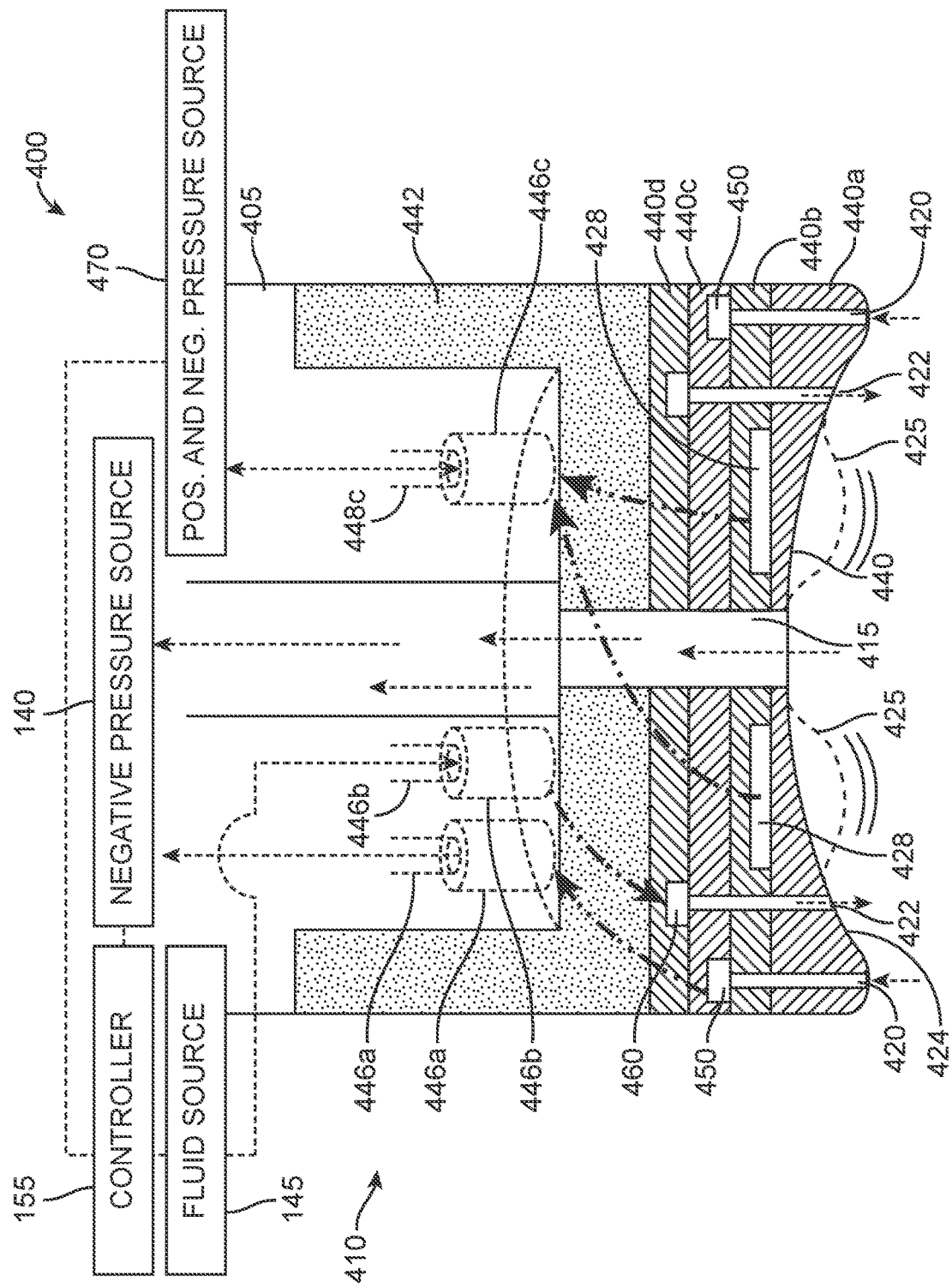
FIG. 11A is a sectional view of the working end of FIG. 10 in a first position showing fluid inflow channels and the suction channels with the elastomeric actuators in a repose or non-actuated position.
Figure 11B:
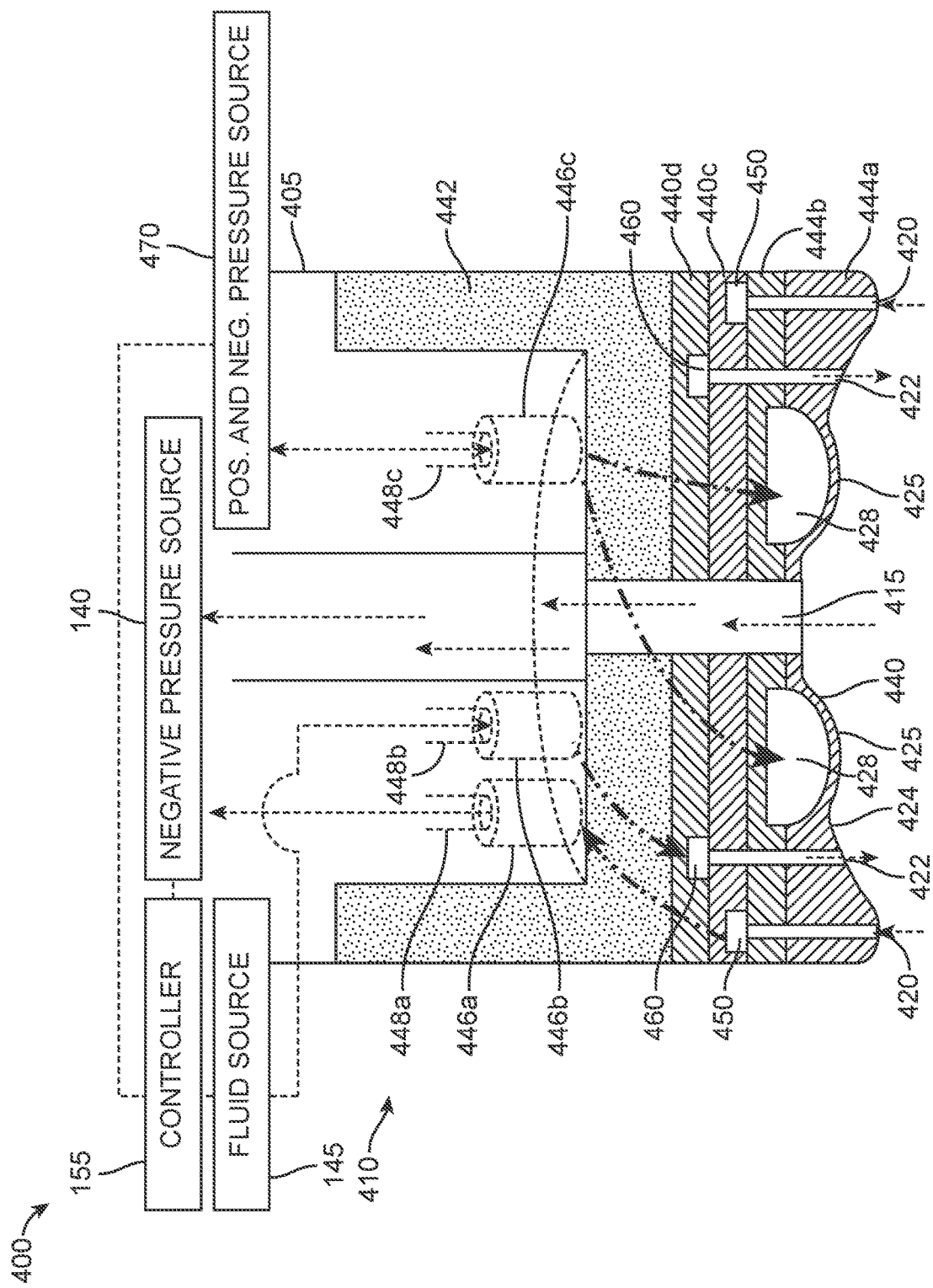
FIG. 11B is a sectional view as in FIG. 11A in a second position showing the elastomeric actuators in an actuated position.

FIGS. 10 and 11A-11B illustrate another variation of fluid-assisted microdermabrasion system 400 that utilizes a handheld device as described above with body 405 and an applicator tip 410 that utilizes a fluidic actuator instead of a linear resonant actuator or LRA 175 as describe above. In general, the applicator tip variations of FIGS. 10 and 11A-11B again are disposable tips with a central aspiration pathway passageway 415, a peripheral aspiration ports 420, and the plurality of fluid outflow ports 422 in the skin contact surface 424 as described previously. In addition, the applicator tip 410 includes one or more fluid actuators 425 which comprise pneumatic or hydraulic expandable interior chambers 428 that can actuate an elastomeric surface portion 440 of the applicator tip 410 as shown in FIGS. 11A-11B. There may be a single annular actuator or up to 20 or more actuators 425 in the skin contact surface 424. The actuators 425 of the type shown have "high amplitude" capabilities, when compared to amplitude of linear resonant actuators or sonic/ultrasonic skin treatment devices. Further, the frequency of actuation can be adjustable over a very wide range, for example from less than 1 Hz to 50 Hz or more.

Of particular interest, the applicator tip 410 comprises a microfabricated microfluidic body which can be manufactured by "soft lithography" means as is known in the art. There are several different techniques of microfabricating fluidic devices—all collectively known as soft lithography. For example, microtransfer molding is used wherein a transparent, elastomeric polydimethylsiloxane (PDMS) stamp has patterned relief on its surface to generate features in the polymer. The PDMS stamp is filled with a prepolymer or ceramic precursor and placed on a substrate. The material is cured and the stamp is removed. The technique generates features as small as 250 nm. Replica molding is a similar process wherein a PDMS stamp is cast against a conventionally patterned master. A polyurethane or other polymer is then molded against the secondary PDMS master. In this way, multiple copies can be made without damaging the original master. The technique can replicate features as small as 30 nm. Another process is known as micromolding in capillaries (MIMIC) wherein continuous channels are formed when a PDMS stamp is brought into conformal contact with a solid substrate. Then, capillary action fills the channels with a polymer precursor. The polymer is cured and the stamp is removed. MIMIC can generate features down to 1 μm in size. Solvent-assisted microcontact molding (SAMIM) is also known wherein a small amount of solvent is spread on a patterned PDMS stamp and the stamp is placed on a polymer, such as photoresist. The solvent swells the polymer and causes it to expand to fill the surface relief of the stamp. Features as small as 60 nm have been produced (see Xia and Whitesides, Annu. Rev. Mater. Sci. 1998 28:153-84).

Referring to FIG. 11A, it can be seen that the disposable soft lithography applicator tip 410 includes a base portion 442 of a rigid plastic for coupling with a device body 405, and plurality of microfabricated elastomer layers 444a-444d that include microfluidic channels, features, and components. In this variation, there are four elastomer layers 444a-444d, but it should be appreciated that there can be from 2 to 20 or more elastomer layers. As can be seen in FIGS. 10 and 11A, the applicator tip 410 has male flow connectors 446a-446c that couple with flow channels 448a-448c in the device body 442. For example, male connector 446a connects with flow channel 448a in body 405 that in turn communicates with the annular channel 450 and peripheral aspiration ports 420. FIG. 11A further shows flow channel 448a extends through the device body 405 and is operatively coupled to the negative pressure source 140. It can be understood that annular channel 450 in the fluidic tip 410 then communicates with a plurality of peripheral aspiration ports 420.

FIGS. 11A-11B further shows that male flow connector 446b couples with flow channel 448b in the device body and fluid source 145 to provide fluid flows to the skin contact surface 424 through outflow ports 422. Again, the male connector 446b connects with an annular channel 460 that extends around the applicator tip 410 to communicate with the ports 422.

Still referring to FIGS. 11A-11B, the system 400 includes a reversible pump system or positive and negative pressure source 470 for actuating the actuators 425. In one variation, the pump system 470 can be an electro-mechanical pressure generator, such as an AC or a DC air pump. When operating to provide a vacuum or positive pressure, the source 470 can generate between 1 and 14 psi of force, for example. The pump system 470 can be a piston pump, or other pump type coupled to controller 155 that can deliver a precise limited volume of fluid pressure to the one more actuators 425. In FIGS. 11A-11B, the male flow connector 446c couples with flow channel 448c in body 442 and pressure source 470 to provide gas (or liquid) flows to chambers 428 of the actuators 425. The actuation of pressure source 470 and the actuators 425 is controlled by controller 155, which is synchronized with activation of the negative pressure source 140 and fluid source 145. In one variation, the operator depresses a trigger and the controller 155 activates the negative pressure source 140 to suction the patient's skin against the skin contact surface 424. The suction forces can draw fluid through ports 422 to the skin interface, or the controller 155 can release the fluid from source 145 a selected time interval later by controlling a valve. Thereafter, the operator can depress a trigger further (or actuate another trigger) to actuate the actuators 425. In one variation, the actuators 425 are controlled by controller 155 to operate at a predetermined frequency and amplitude. In another variation, the controller 155 can be configured to allow the operator to select from a multitude of actuator frequencies and amplitudes, for example on a touch screen of the controller 155.

In use, the system 400 of FIGS. 10-11B would allow the operator to strongly suction the patient's skin against the skin contact surface 424 which will tension and stretch the engaged skin, and then the actuation of the actuators 425 will further tension and stretch the skin in the presence In another variation, the skin contact surface 424 can have abrasive elements (e.g., diamond particles, and the actuation of the actuators can cause motion in the abrasive over the patient's skin. This can be done in combination with a fluid infusion treatment.

Figure 12A:
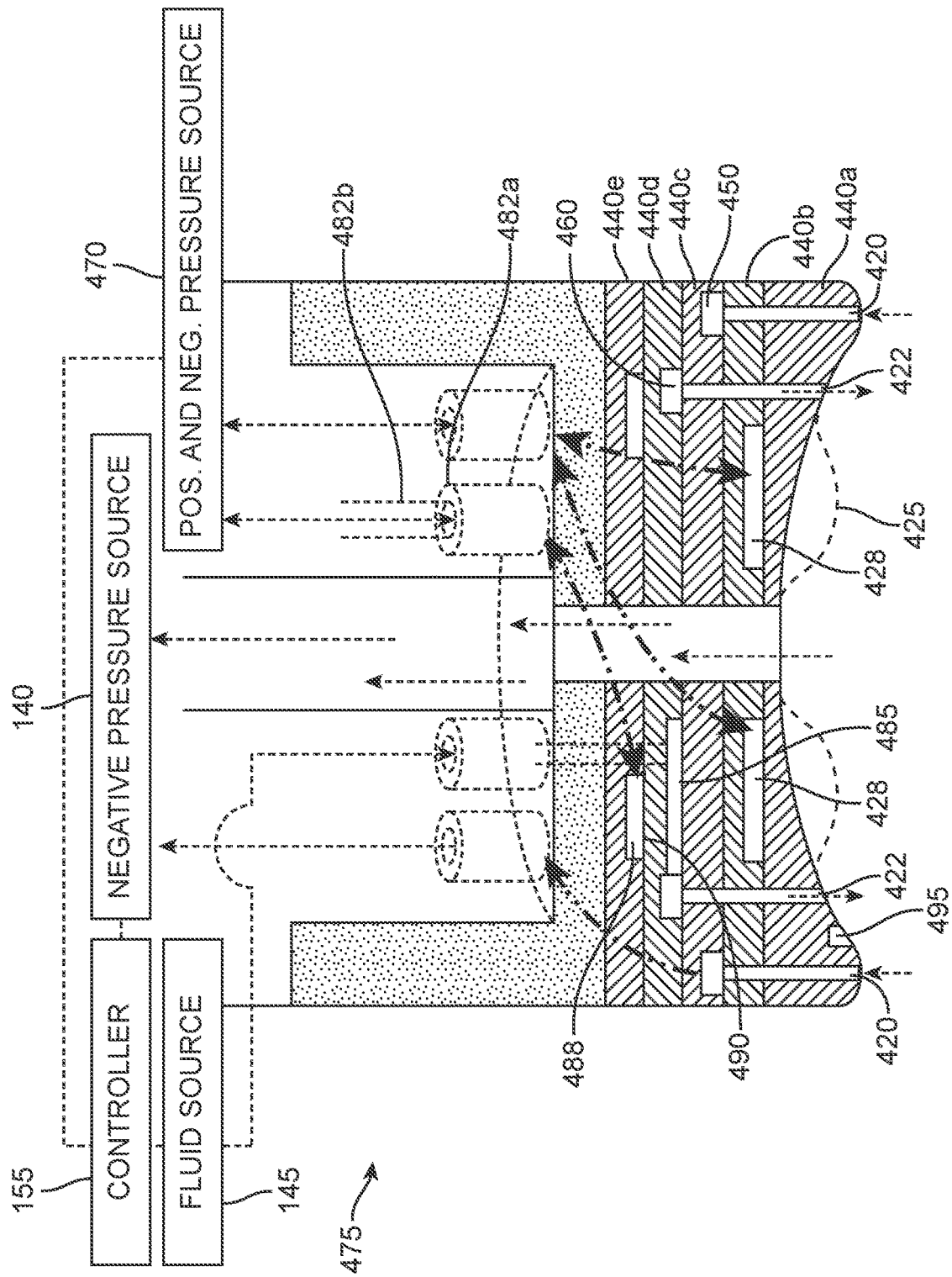
FIG. 12A is a sectional view of a working end similar to that of FIGS. 11A-11B with a microfabricated elastomeric valve operated by a controller to control fluid inflows, with the valve in a normally open position.

FIGS. 12A-12B illustrate another soft lithography applicator tip 475 that is similar to the embodiment of FIGS. 10-11B with actuators 425, fluid infusion channels 422 and aspiration channels 420 and 440. The tip 475 differs in that is includes an additional feature comprising at least one fluidic valve 480 in elastomer layers 440a-440e of the tip. In FIG. 12A, it ca be seen that a male flow connector 482a couples with flow channel 482b in the device body and communicates with pressure source 470 operated by the controller 155 to and open and close an elastomeric valve 480. In this variation, the valve 480 opens and closes fluid flow channel 485 formed in the elastomer layers 440c-440d that communicates with fluid source 145. More in particular, the valve 480 operates by fluid (typically air) being pumped into chamber 488 by pressure source 470 which expands chamber 488 to cause elastomer wall 490 of layer 440d to impinge on and close flow channel 485 which communicates with annular channel 460 and the flow ports 422 in the skin contact surface 424. FIG. 12A shows valve 480 in an open position and FIG. 12A shows valve 480 in a closed position. In can be understood that controller 155 then operate the valve 480 to control delivery of therapeutics fluids from source 145 to the skin interface in cooperation with actuation of the actuators 425 and aspiration forces. The valve 480 can be used to conserve therapeutic fluids or to only introduce fluid when needed and can be operated manually or by the controller 155. A sensor, such as capacitance sensor 495 shown in FIGS. 12A-12B, can be coupled to controller 155 and can sense when whether the skin interface has adequate or inadequate fluid flows for a particular skin treatment. An applicator tip similar to that of FIGS. 12A-2B can be configured with a plurality of valves 480 or gates to direct flows from different fluid sources can be used, and such valves and gate can allow for computer control all operational parameters in all the channels. It should be appreciate that other forms of valves, normally open valves, normally closed valves, gates, one-way valves, check valves, pressure relief valves, flow control mechanisms and the like can be fabricated in an applicator tip 475 from elastomeric materials for obvious purposes of controlling and modulating flows in hydraulic and/or pneumatic circuits, and such elements can be of types used in fluidic chip fabrications and described in U.S. Pat. Nos. 6,951,632; 6,953,058; 6,802, 342; 8,590,573; 8,104,514; 7,640,947; 7,392,827 and 6,829, 753 which are incorporated herein by this reference.

Figure 13B:
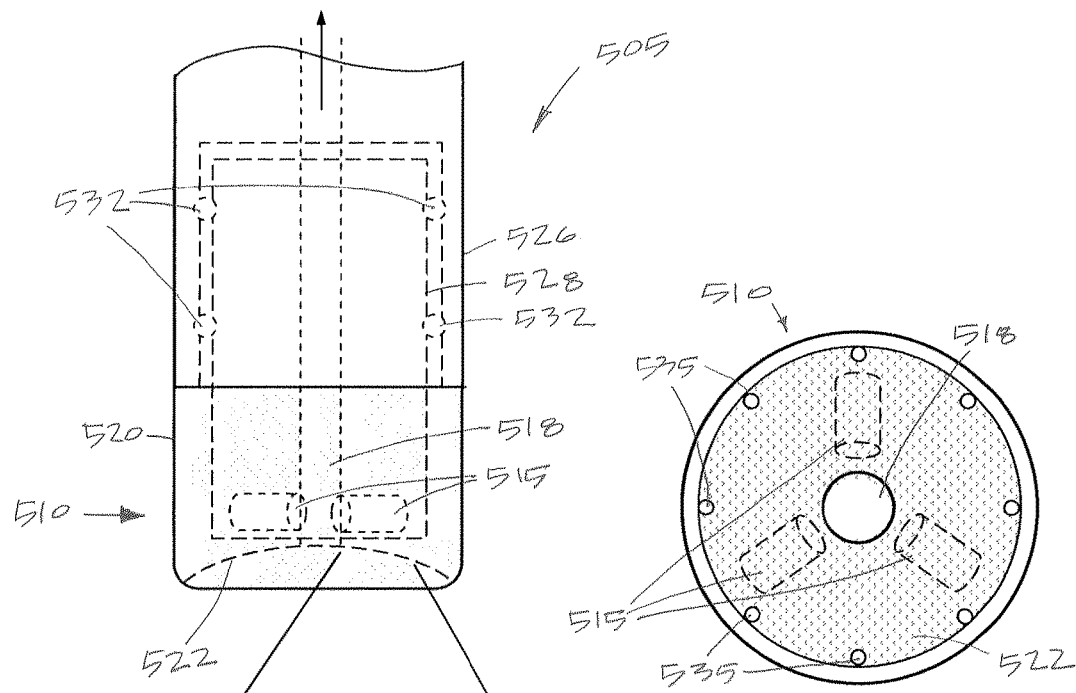
FIG. 13B is an end view of the working end of FIG. 13A.
Figure 13A:
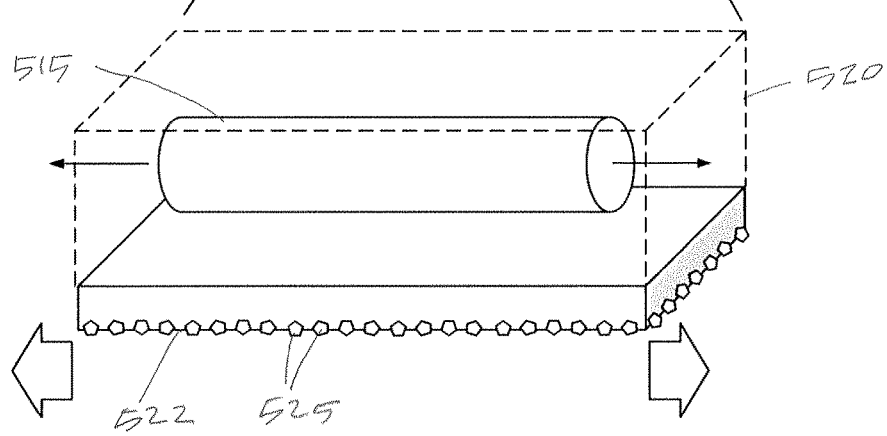
FIG. 13A is a schematic view of another variation of a working end with a floating component for maximizing the delivery of vibrational forces to a patient's skin.

FIGS. 13A-13B illustrate another variation in which a hand-held device 505 has a working end 510 that again carries at least one LRA 515 disposed around a central aspiration channel 518. The disposable applicator tip 520 is fabricated of an elastomer with a skin contact surface 522 having abrasive elements 525 disposed thereon. The LRAs 515 are adapted to stretch and impart motion to the skin to skin contact surface 522 parallel to the surface of the skin. In this variation, the device body 526 includes a floating body component 528 that carries the LRA's. It can be seen in FIG. 13A that soft resilient O-rings 532 carry the floating, vibrating body component within the device body 526. This allows for optimal transmission of vibration forces to the skin contact surface 522 and also prevents vibration of the device body 526.

In one variation shown in FIGS. 13A-13B, the working end carries three LRA's 515 with fluid inflow ports 535 and the fluid outflow channel 518 as described previously. In another variation, the floating body component 528 can carry first linear actuators to deliver forces for abrasion parallel to the skin and second linear actuators for to deliver forces perpendicular to the skin for fluid infusion. For example, a device can be similar to that of FIG. 8, with two LRA's for providing the abrasion mode, and a single LRA (e.g., a coin LRA) can be used to drive fluids into the patient's skin. In a variation, the fluid reservoir also can be carried in the handle and the user can simply squeeze a flexible fluid reservoir to provide for fluid infusion pressure. In one variation, the aspiration source can be coupled to the handle to make the entire system portable. In this variation, the only umbilical that is needed is a conduit to the negative pressure source which is configured to suction the patient's skin into the skin contact surface.

In another variation, an ultrasound wave generator such as a piezoelectric crystal can be provided in the working end to deliver waves at ultrasonic speeds to the skin, for example, in the range of 1 Mhz to 6 Mhz. In another variation, the working end can include components and electrodes for delivering electrical current to the skin of a patient. In a further variation, the working end can be provided with a source of light energy, such as an LED or a flash lamp or deliver light energy to the patient's skin, for example visible or infrared light. In one variation, a UV light from an LED is provided to kill bacteria. Another variation can include a plurality of microneedles in the skin contact surface for creating microperforations in the skin, in order to deliver fluids or electrical currents into the patient's skin.

It should be appreciated that the treatment fluids can consist of water or an aqueous solution containing medications, peeling agents, serums, nourishing agents, botanicals, plumping agents, vitamins, hormones and the like known for topical use.

Figures 14A, 14B:
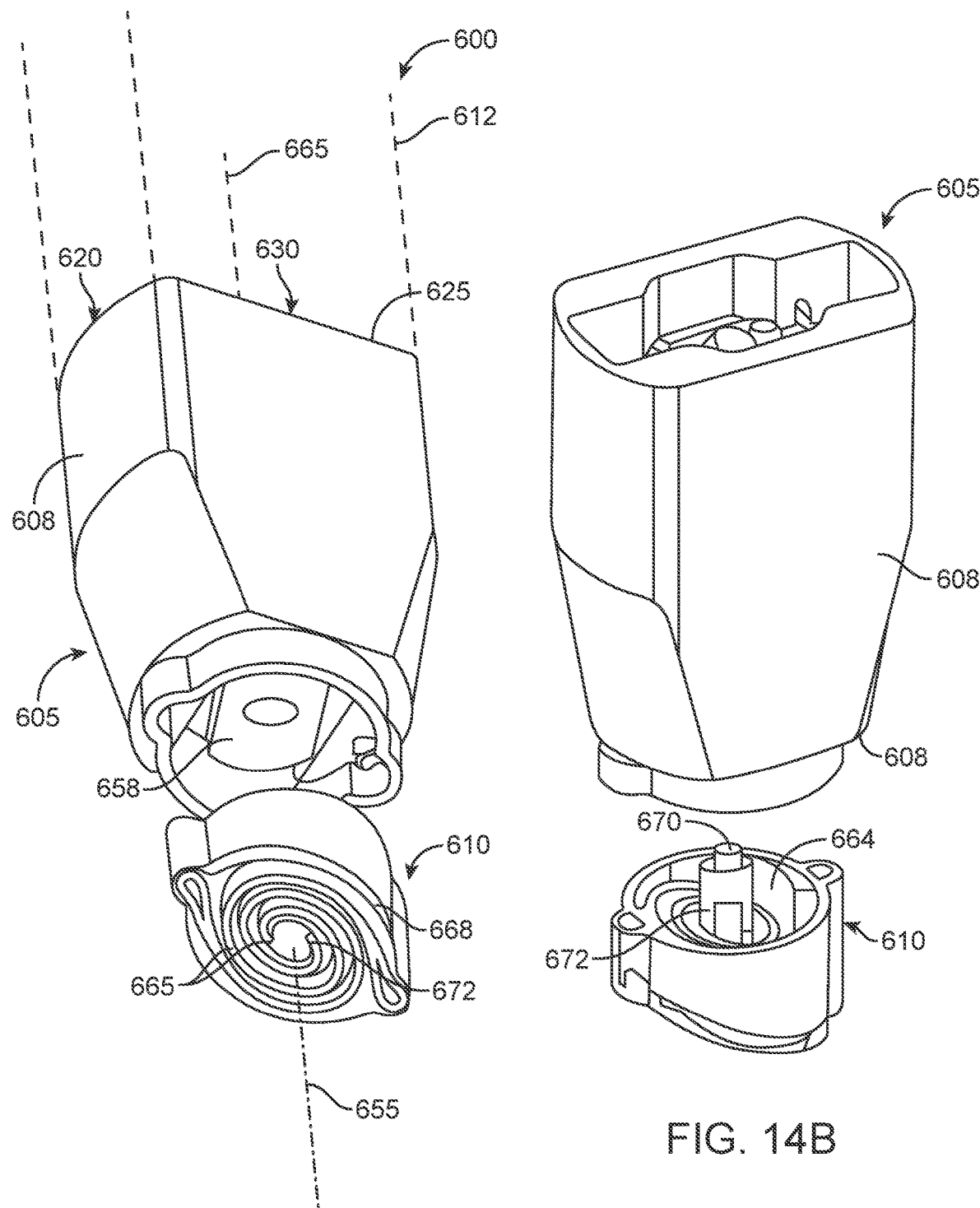
FIG. 14A illustrates a working end of another variation of a skin treatment system that includes a single use distal tip that can be actuated by a motor drive and further includes fluid inflow and fluid outflow components.
FIG. 14B is another view of the working end of FIG. 14A from a different angle.

FIGS. 14A-17 illustrate another variation of a skin treatment system 600. As can be seen in FIGS. 14A-14B, a working end 605 with housing 608 and a distal skin-interfacing tip or applicator tip 610 is shown with a handle portion 612 in phantom view. The handle can be held like a pencil as shown in the embodiment of FIG. 1. The variation of FIGS. 14A-17 again includes a fluid source 620, and negative pressure source 625 and a power source 630, such as an electrical source for operating an actuation mechanism in the distal tip 610 that interfaces and engages a patient's skin.

Figure 23:
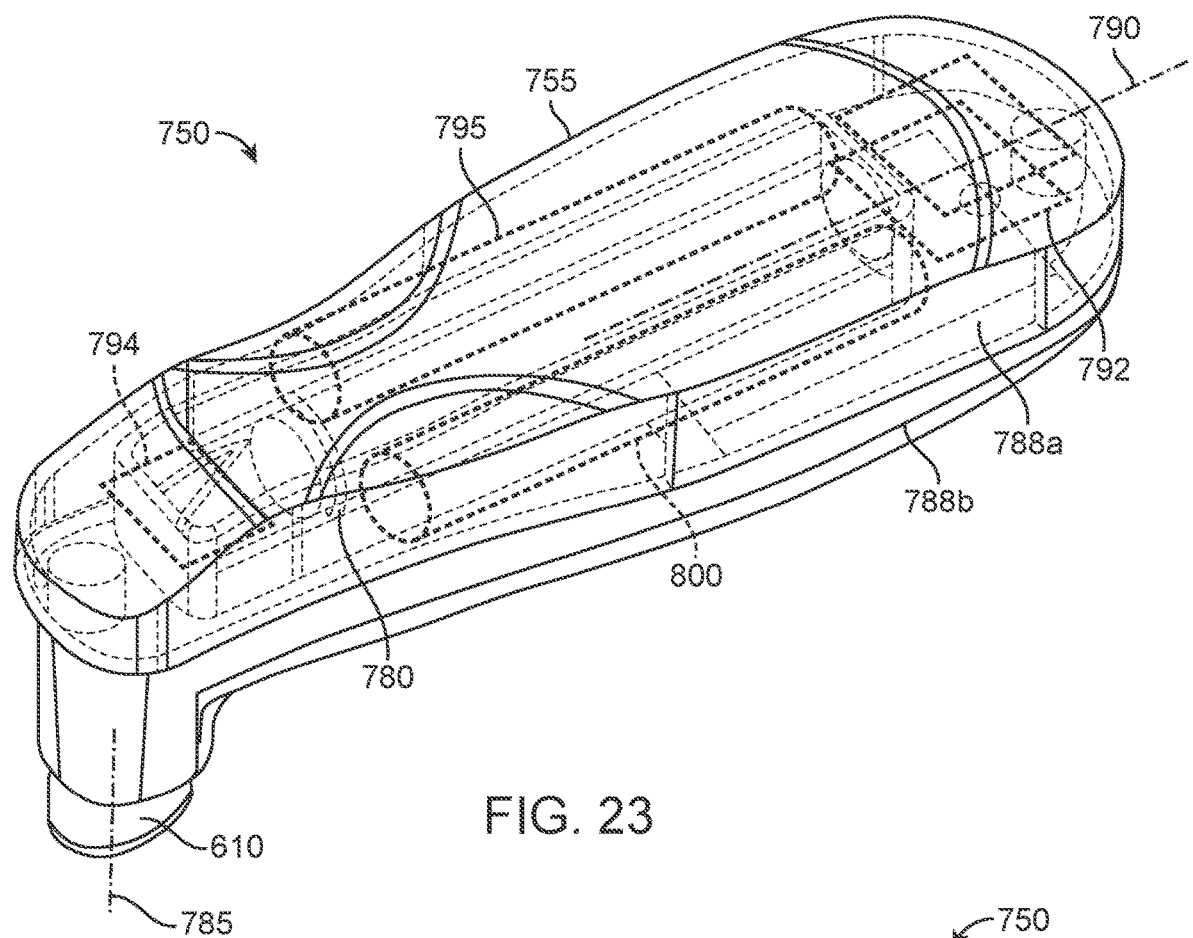
FIG. 23 is a perspective view of another variation of a skin treatment system that comprises a hand-held device with a single use distal tip wherein the handpiece alone carries a fluid source, a motor drive for actuating the working end, a pump source for negative pressure and a battery/accumulator cell as a power source.
Figure 24:
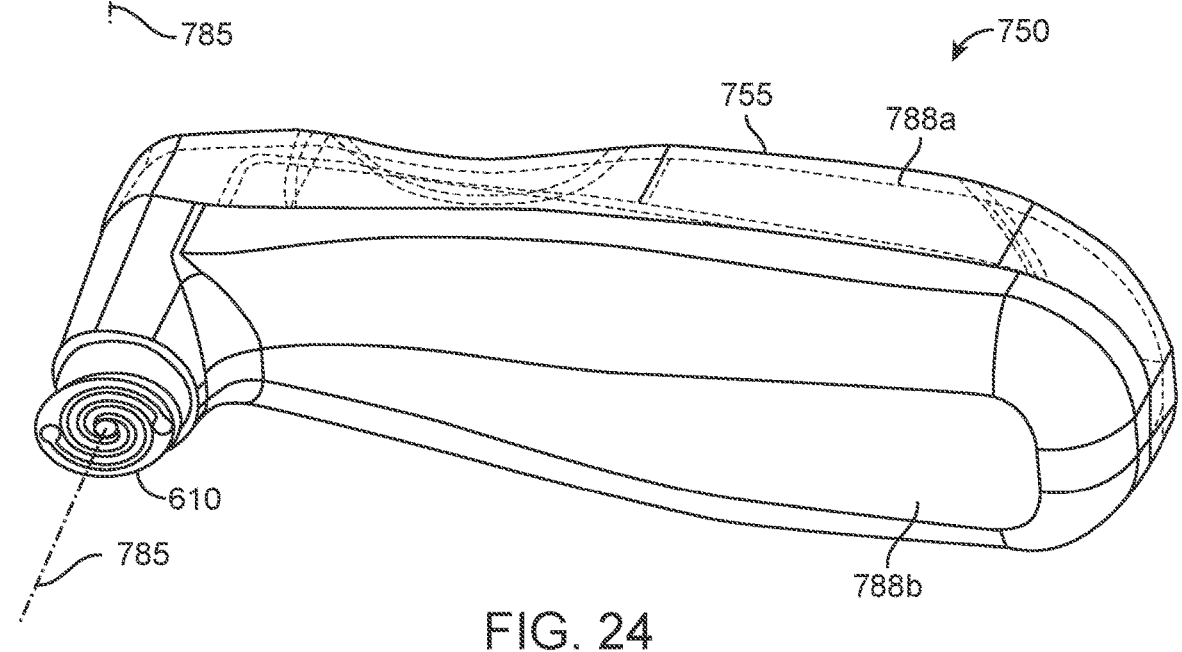
FIG. 24 is a perspective view of the hand-held system of FIG. 23 from a different angle illustrates another.

In the variation shown in FIGS. 14A-17, the fluid source 620, negative pressure source 625, and electrical source 630 can be remote from the handle portion 612 as described in previous embodiments. In another variation shown below in FIGS. 23-24, it should be appreciated that a fluid source 620, negative pressure source 625 and an electrical source 630 can be provided within the form factor of its handpiece. Such an alternative skin treatment system of FIGS. 23-24 is suited for consumer or home use.

Figure 15:
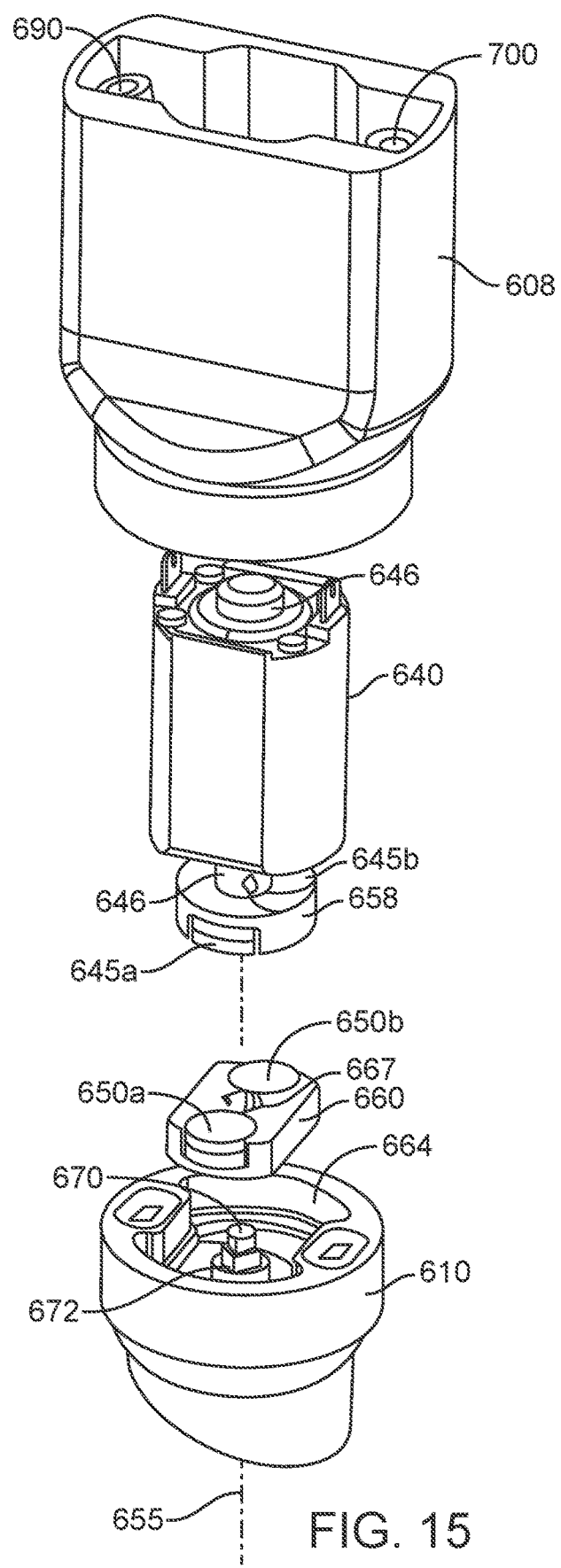
FIG. 15 is an exploded view of the working end of FIGS. 14A-14B.
Figure 16:
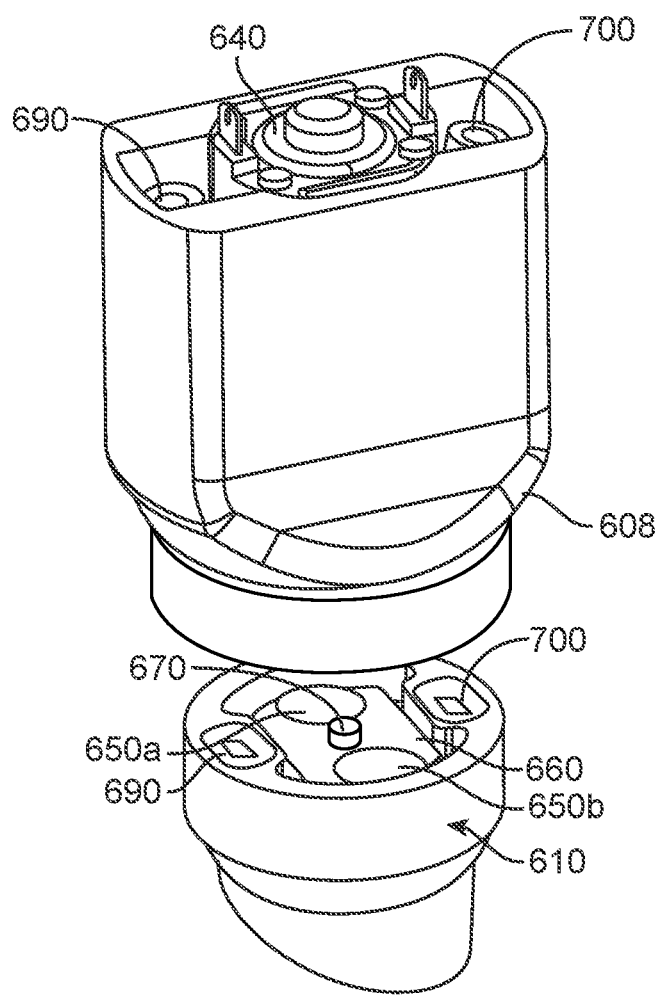
FIG. 16 is another exploded view of the working end of FIGS. 14A-14B.

In the system variation of FIGS. 14A-17, the mechanism that is adapted to actuate the applicator tip 610 comprises a motor drive 640 (FIGS. 15-16) which rotates first and second drive magnets 645a and 645b about the shaft 646 of the motor drive 640. The rotating drive magnets 645a and 645b are carried by rotating magnet-carrying block 658 and are adapted to move or actuate third and forth actuator magnets 650a and 650b that engage the applicator tip 610. As can be seen best in FIG. 15 and FIG. 16, the first and second magnets 645a, 645b are spaced apart and offset from axis 655 of shaft 646 and can influence the actuator magnets 650a, 650b as the magnet-carrying block 658 rotates about axis 655. The actuator magnets 650a and 650b shown in FIGS. 15-16 are also offset from axis 655 in the carried in a magnet holder 660 which partially rotates or oscillates in a receiving space 664 in the tip 610. The magnet holder 660 has a keyed central slot 667 that receives a keyed shaft element 670 in the applicator tip 610. Thus, can be seen how rotation of the drive magnets 645a, 645b can influence, repulse and oscillate the actuator magnets 650a, 650b that then can move or oscillate within the receiving space 664 and actuate the spiral elements 665 of the applicator tip 610 described below.

Figure 17:
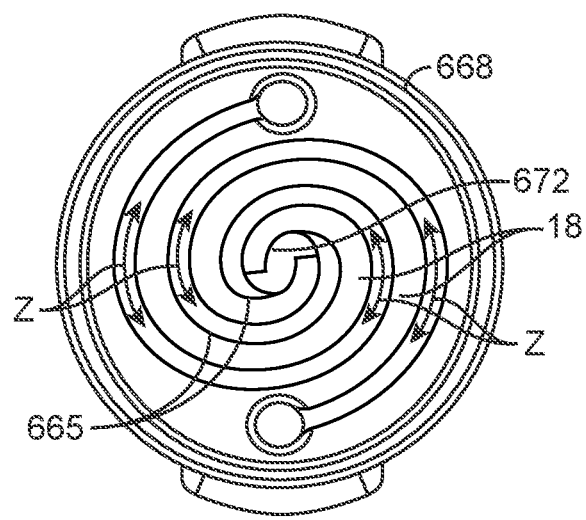
FIG. 17 is an end view of the distal tip of the working end of FIGS. 14A-14B.

Now turning to FIGS. 14A and 17, the applicator tip 610 can be described in more detail. The applicator tip 610 can be molded from a resilient plastic material with a plurality of spiral elements 665 that are deformable and spring-like and move as shown by arrows Z in FIG. 17. In the variation shown in FIG. 17, the actuatable portion comprises two spiral elements 665 that extend from a more rigid periphery 668 of the applicator tip 610 to a central shaft portion 672 that engages the magnet holder 660. Thus, it can be understood that the central shaft portion 672 of applicator tip 610 can be rotated from 10° to about 90°, which will deform, or twist, and move spiral elements as the actuator magnets 650a and 650b oscillate. One advantage of the use of the electrical motor drive 640 is that operation is effectively silent.

FIGS. 14A-14B shows that the applicator tip 610 is removable and disposable. FIGS. 15-16 show the assembly in exploded views. In FIG. 15, the actuator magnets 650a, 650b can be seen in receiving space 664 within the applicator tip 610. In FIG. 16, the actuator magnets 650a, 650b are shown in an exploded view separated from the applicator tip 610. FIG. 16 further shows the motor drive unit 640 separated from the housing 608.

Figure 18:
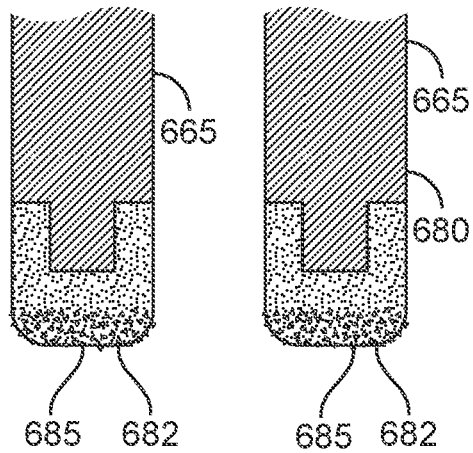
FIG. 18 is an enlarged view of a portion of the distal tip of FIG. 17.

FIG. 17 is an enlarged view of the working end 605 showing a plurality of spiral elements 665 that are actuated by the system. In one variation, the applicator tip 610 comprises an injection molded plastic and can include or skin interface of a lubricious molded silicone or similar elastomer. In a variation shown in FIG. 18, the distal portion 680 of spiral elements 665 comprise a lower durometer silicone 682 that is embedded with diamond particles 685 for abrading the skin as the spiral elements are actuated by the motor drive.

Figure 20:
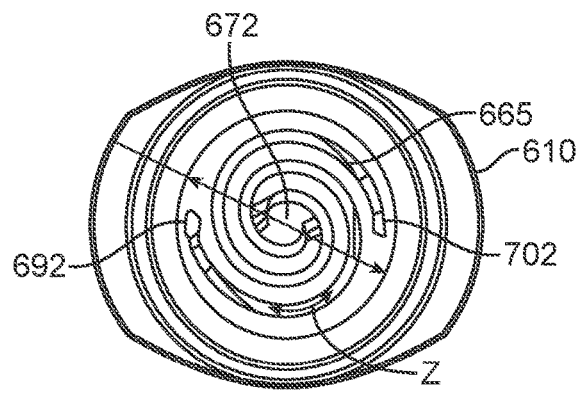
FIG. 20 is another end view of the distal tip of FIGS. 14A-14B.
Figure 21:
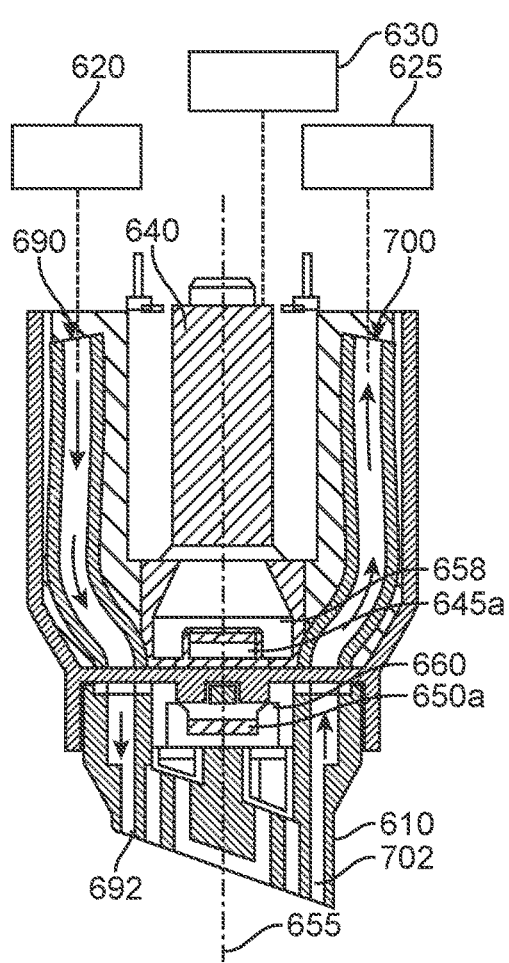
FIG. 21 is a sectional view of the working end of FIGS. 14A-14B.
Figure 22:
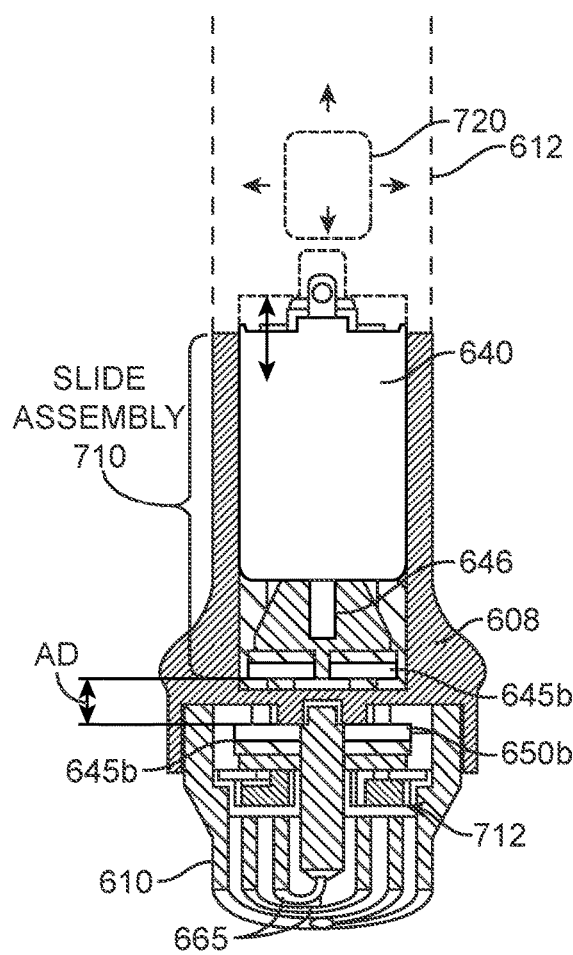
FIG. 22 is another sectional view of the working end of FIGS. 14A-14B rotated 90° from the view of FIG. 21.

As can be understood from the previous embodiments, the system 600 of FIGS. 14A-17 includes fluid inflows and fluid outflows which assist in a skin abrasion treatment, a deep cleansing of the patient's skin, or infusion of fluids into the skin. FIGS. 20-22 show more details of the inflow channels and outflow channels that provide fluid flows into the skin interface. In FIG. 21, it can be seen that fluid inflow channel 690 provides for fluid flows from the fluid source 620 from open channel termination 692 in the applicator tip 610. FIG. 22 further shows a fluid outflow channel 700 with port 702 in the tip 610 which communicates with negative pressure source 625 and is adapted to aspirate fluid away from the skin interface. In FIGS. 21-22, it can further can be seen how the proximity of drive magnets 645a, 645b to the actuator magnets 650a, 650b are provided.

In one variation, the handle 612 includes a slide assembly 710 (see FIG. 22) that carries the drive magnets 650a, 650b and rotating magnet holder 658 (or the assembly of motor 640 and drive magnets) that allows axial movement of the slidable component or assembly 710 within handle 612 and housing 608 over an amplification distance AD shown in FIG. 22. Thus, the drive magnets 645a, 645b can be moved relative to the actuator magnets 650a, 650b to adjust actuation forces. As can be easily understood, the attraction and repulsions forces provided by drive magnets 645a, 645b on the actuator magnets 650a, 650b is proportional to the distance AD between the drive magnets 645a, 645b and the actuator magnets 650a, 650b. In one variation, the sliding mechanism can be spring-loaded to be urged toward less-amplified forces on the applicator tip 610. This embodiment then can have a finger-actuated slider in the handle 612 to move the drive magnets 645a, 645b distally to be in close proximity to the actuator magnets 650a, 650b, to thereby provide maximum actuation forces. FIGS. 20 and 21 show the inflow channel 690 and the outflow channel 700 and open terminations 692, 702 in the perimeter of the tip 610 but it should be appreciated that the inflow and outflow channels can be positioned in various regions of the applicator tip 610.

FIGS. 21 and 22 also illustrate a silicone seal 712 between the disposable tip 610 and the housing 608.

In one variation, the handle 612 may have a finger actuated switch 720, similar to a joystick, that would allow multiple functions depending on movement of the switch 720 (See FIG. 22). For example, the switch 720 could be slidable in an axial direction to increase or decrease the amplitude of the force is applied to the actuator tip 610. Radially inward depression of the switch 720 can increase the frequency of the actuation by changing the speed of the motor drive 640. Further, movement of the switch from side to side could modulate the negative pressure (pump speed) applied through the system which would increase or decrease fluid flows to and from the applicator tip 610. In other words, a single finger actuated switch a button on the handle can be used to modulate three functions: amplitude of actuation, frequency of actuation, and fluid flow through the system.

Figure 19A:
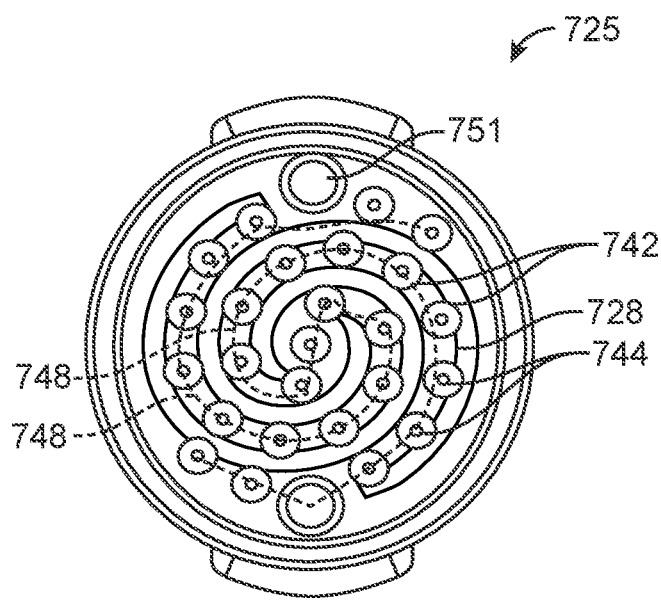
FIG. 19A is an end view of an alternative distal tip of a working end that can be fitted to the housing of FIGS. 14A-14B.
Figure 19B:
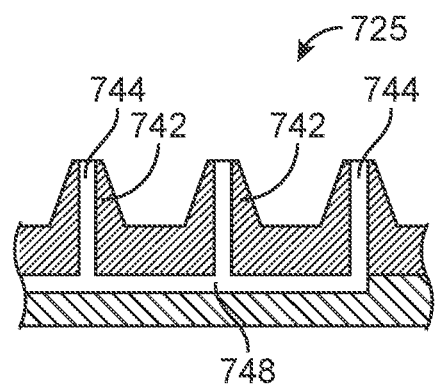
FIG. 19B is an enlarged view of a portion of the distal tip of FIG. 19A.

FIGS. 19A-19B show another tip 725 that can be fitted to the housing 608 of FIG. 14A-22 and cooperates with the drive magnets and actuator magnets as described previously. In this variation, the skin interface again is actuated but the surface 728 is continuous with a plurality of projecting elements 742 and inflow ports 744 therein for fluid inflows to the skin. The fluid outflow port 751 for aspirating fluid from the skin interface. Such an applicator tip 725 is adapted for skin cleansing and can optionally have abrasive particles, such as diamond dust, carried by the projecting elements 742. It can be understood how the fluid inflow channel 690 and housing 608 can be coupled to a flow channel in applicator tip 725 that communicates with microchannels 748 that extend to each of the inflow ports 744 (FIG. 19B).

FIGS. 23-24 illustrate a system 750 that carries all the fluid treatment components in a handheld device or handpiece 755. The handpiece 755 of FIGS. 23-24 can use an applicator tip 610 together with an electric motor 780 and magnetic drive mechanism as shown in FIGS. 14A-16 with a right angle or flex-drive since the shaft of motor 780 in the handpiece 755 is not aligned with the axis 785 of the rotating and actuated magnets in applicator tip 610.

In FIGS. 23-24, the housing of handpiece 755 carries the motor 780 centrally along handle axis 790 of the handpiece. A battery 792 is also carried within the housing 788. A pump 794 is provided for fluid flows. A fluid source 795 is provided which can comprise a tubular fluid cartridge or a flexible thin wall packet. On the other side of the motor 780, a fluid collection reservoir 800 is provided which can comprise a thin-wall packet or a sponge material in chamber of the housing that is adapted to receive fluid that has circulated through the distal tip 610. In one variation, the housing can comprise sides 788a and 788b of the handpiece 755 that can be separated into opposing halves to insert the fluid source packet or cartridge 795 and to remove the collection reservoir packet 800. In other respects, the system can function as described previously wherein the diaphragm pump can suction fluid from the fluid source 795 through the skin interface to the collection reservoir 800.

Figure 25:
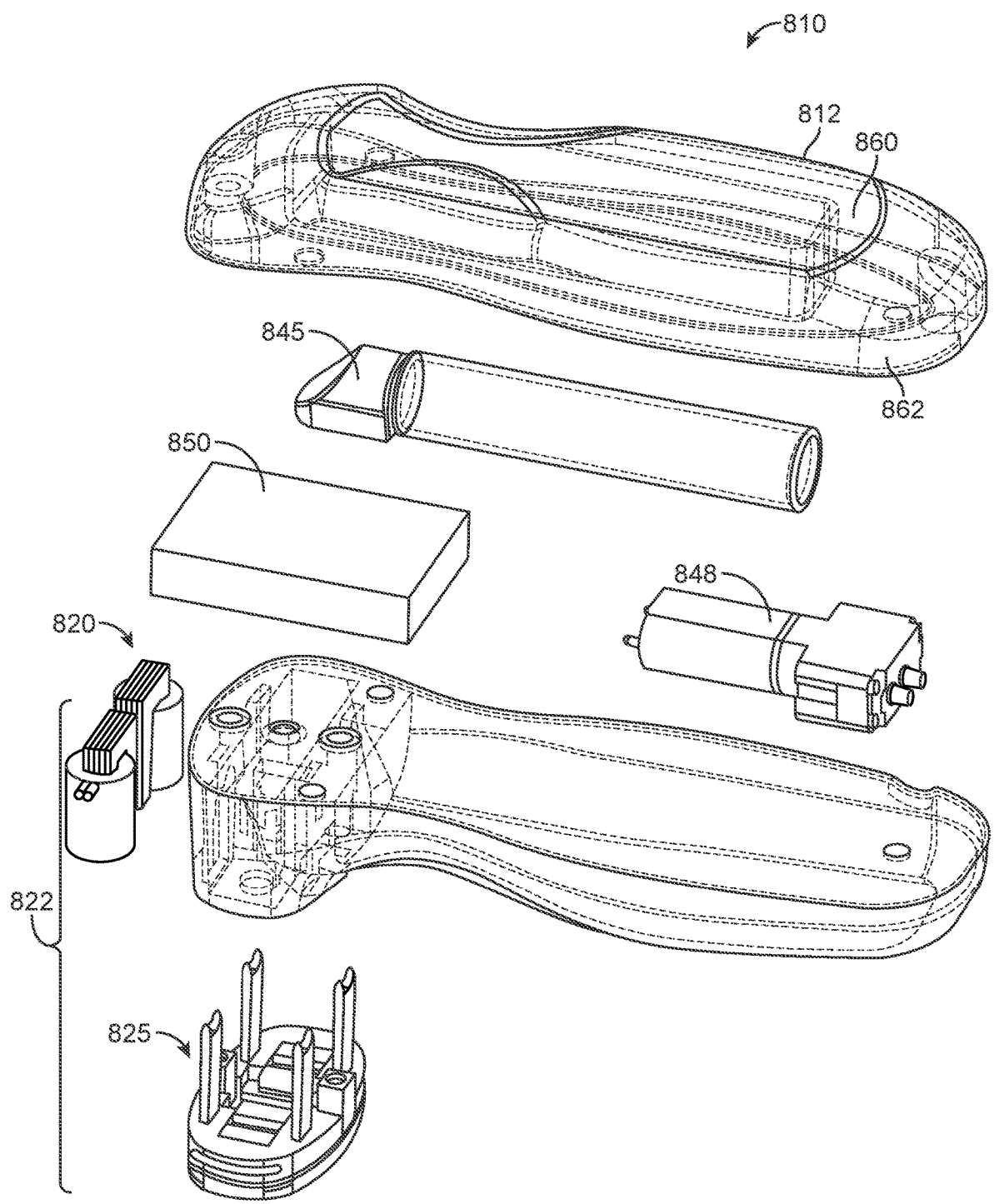
FIG. 25 is a perspective view of an alternative hand-held system which again carries a fluid source, a pump source for negative pressure and a battery/accumulator cell as a power source, but includes actuators for actuating the skin interface.

FIG. 25 illustrates another hand-held system 810 that has a handpiece 812 that carries actuators 820 in the working end 822 that functions in a similar manner as the embodiments of FIGS. 1-10 above, rather than an electric motor as shown in the variation of FIGS. 23-24. In FIG. 25, the single-use disposable applicator head 825 is detachable from the 812. Solenoid actuators 820 are shown that apply actuation forces to the applicator head 825. The applicator head 825 then can apply forces in various directions to the patient's skin during fluid delivery as described previously. The interior of the handpiece 812 carries a single-use replaceable fluid source or canister 845 and a micropump indicated at 848. The micropump can be a piston pump, peristaltic pump, diaphragm pump, or solenoid pump. An accumulator cell or battery unit 850 is provided. The spaces in the handle on either side of the fluid source 845 carry a flexible wall sac that functions as a fluid collection reservoir 860. In this variation, the fluid collection reservoir 860 is carried in the plastic disposable portion 862 of the handpiece 812. It should be appreciated in this embodiment, any type of actuator(s) 820 may be used such as a linear actuator, an eccentric rotating mass actuator or a piezoelectric actuator, all of which can provide suitable actuating forces to the skin interface. This variation, the skin interface may be of the type shown in FIGS. 19A-19B.

The invention claimed is:

1. A tissue treatment system, comprising:
   a handpiece having a housing and carrying a distal tip configured to contact a tissue surface, the distal tip comprising a plurality of spaced apart flexible elements extending on the surface of the distal tip from a periphery of the surface towards a central shaft portion of the surface, where the spaced apart flexible elements include an abrasive surface;
   an actuator coupled to the central shaft portion, where the actuator is configured to vibrate to cause movement of the central shaft portion in a reciprocating rotational motion relative to an axis of the distal tip independently of the housing to displace the spaced apart flexible elements to cause the abrasive surface to remove a surface of tissue;
   a first aperture arrangement in the distal tip consisting of at least one port in communication with a treatment media source; and
   a second aperture arrangement in the distal tip consisting of at least one port in communication with a vacuum source for removing treatment media and tissue during a treatment procedure.

2. The tissue treatment system of claim 1, wherein the distal tip is configured for detachable coupling to the handpiece.

3. The tissue treatment system of claim 1, where the plurality of spaced-apart flexible elements extends outward from a center hub of the distal tip such that the reciprocating rotational motion of the distal tip causes the spaced apart flexible elements to move in an arc over the skin of the patient.

4. The tissue treatment system of claim 1, wherein the spaced-apart flexible elements extend in a partial spiral shape outward from the center hub of the distal tip.

5. The tissue treatment system of claim 1, where the spaced-apart flexible elements comprise a plurality of spiral elements that are deformable and spring-like.

6. The tissue treatment system of claim 1, wherein the plurality of spaced apart flexible elements comprise projecting elements.

7. The tissue treatment system of claim 1, where the plurality of spaced apart elements comprise a lower durometer material located at a distal end.

8. The tissue treatment system of claim 1, where the plurality of spaced apart elements comprises a plurality of abrasive elements.

9. The tissue treatment system of claim 1, wherein the actuator includes a plurality of drive magnets and a plurality of actuator magnets, where the plurality of drive magnets and the plurality of actuator magnets are offset from a central axis of the central shaft portion, the plurality of actuator magnets are coupled to the central shaft portion such that movement of the plurality of drive magnets causes movement of the plurality of actuator magnets to cause rotational actuation of the central portion.

* * * * *